(12) United States Patent
Shaikh et al.

(10) Patent No.: US 10,858,327 B2
(45) Date of Patent: Dec. 8, 2020

(54) METHOD OF HYDROGENATING A COMPOUND HAVING AN N-HETEROCYCLIC AROMATIC RING

(71) Applicant: KING FAHD UNIVERSITY OF PETROLEUM AND MINERALS, Dhahran (SA)

(72) Inventors: M. Nasiruzzaman Shaikh, Dhahran (SA); Zain H. Yamani, Dhahran (SA)

(73) Assignee: KING FAHD UNIVERSITY OF PETROLEUM AND MINERALS, Dhahran (SA)

(\*) Notice: Subject to any disclaimer, the term of this patent is extended or adjusted under 35 U.S.C. 154(b) by 0 days.

(21) Appl. No.: 16/790,150

(22) Filed: Feb. 13, 2020

(65) Prior Publication Data

US 2020/0309339 A1 Oct. 1, 2020

Related U.S. Application Data

(63) Continuation of application No. 16/366,586, filed on Mar. 27, 2019, now Pat. No. 10,618,878.

(51) Int. Cl.
| | |
|---|---|
| *C07D 295/023* | (2006.01) |
| *B01J 37/03* | (2006.01) |
| *B01J 23/46* | (2006.01) |
| *B01J 23/745* | (2006.01) |

(52) U.S. Cl.
CPC ........ *C07D 295/023* (2013.01); *B01J 23/464* (2013.01); *B01J 23/745* (2013.01); *B01J 37/035* (2013.01)

(58) Field of Classification Search
CPC ...... B01J 23/464; B01J 23/745; B01J 37/035; C07D 295/023
USPC ........................................................ 362/521
See application file for complete search history.

(56) References Cited

U.S. PATENT DOCUMENTS

| | | | |
|---|---|---|---|
| 5,753,584 | A | 5/1998 | Paez et al. |
| 7,732,634 | B2 | 6/2010 | Soled et al. |
| 8,211,486 | B2 | 7/2012 | Beers et al. |
| 9,480,978 | B1 | 11/2016 | Shaikh et al. |
| 10,125,159 | B2 * | 11/2018 | Shaikh .................... C07F 15/02 |
| 10,370,397 | B2 * | 8/2019 | Shaikh .................. C07C 45/505 |
| 10,463,391 | B2 * | 11/2019 | Shaikh .................... C07F 17/02 |

(Continued)

FOREIGN PATENT DOCUMENTS

CN 1272308 C 8/2006

OTHER PUBLICATIONS

Carl-Hugo Pélisson, et al, "Magnetically Retrievable Rh(0) Nanocomposite as Relevant Catalyst for Mild Hydrogenation of Functionalized Arenes in Water", ACS Sustainable Chemistry & Engineering, vol. 4, No. 3, 2016, pp. 1834-1839 (Abstract Only).

(Continued)

*Primary Examiner* — Christopher M Raabe
(74) *Attorney, Agent, or Firm* — Oblon, McClelland, Maier & Neustadt, L.L.P.

(57) ABSTRACT

A method of reducing an aromatic ring under relatively mild condition using sub-nano particles of a transition metal supported on super paramagnetic iron oxide nanoparticles (SPIONs). The catalyst is efficient for catalyzing the reduction of both carbocyclic and heterocyclic compound. In compound comprising both carbocyclic and heterocyclic aromatic rings, the catalyst displays high regioselectivity for the heterocyclic ring.

2 Claims, 15 Drawing Sheets

(56) References Cited

U.S. PATENT DOCUMENTS

| | | | |
|---|---|---|---|
| 10,618,878 B1* | 4/2020 | Shaikh | C07D 295/023 |
| 2018/0099987 A1* | 4/2018 | Shaikh | A61B 17/22 |
| 2019/0029718 A1* | 1/2019 | Shaikh | B01J 37/0203 |
| 2019/0031697 A1* | 1/2019 | Shaikh | B01J 31/28 |

OTHER PUBLICATIONS

Aniruddha Biswas, et al., "A Mild Rhodium Catalyzed Direct Synthesis of Quinolones from Pyridones: Application in the Detection of Nitroaromatics", The Journal of Organic Chemistry, vol. 82, No. 20, 2017, pp. 10989-10996 (Abstract Only).

Urszula Laska, et al., "Rhodium Containing Magnetic Nanoparticles: Effective Catalysts for Hydrogenation and the 1,4-Addition of Boronic Acids", Catalysis Letters, vol. 122, Issue 1-2, Apr. 2008, pp. 68-75 (Abstract Only).

M. Nasiruzzaman Shaikh, et al., "Sub-nanometric Rh decorated magnetic nanoparticles as reusable catalysts for nitroarene reduction in water", Catalysis Communications, vol. 119, Jan. 10, 2019, pp. 134-138 (Abstract Only).

Eduardo Baralt, et al., "Homogeneous Catalytic Hydrogenation. 6. Synthetic and Mechanistic Aspects of the Regioselective Reductions of Model Coal Nitrogen, Sulfur, and Oxygen Heteroaromatic Compounds Using the ($\eta^5$-Pentamethylcyclopentadienyl)rhodium Tris(acetonitrile) Dication Complex as the Catalyst Precursor", J. Am. Chem. Soc., vol. 114, No. 13, 1992, pp. 5187-5196.

Hannelore Konnerth, et al., "Selective hydrogenation of N-heterocyclic compounds using Ru nanocatalysts in ionic liquids", Green Chemistry, vol. 19, Mar. 28, 2017, pp. 2762-2767.

Jialin Wen, et al., "Strong Brønsted acid promoted asymmetric hydrogenation of isoquinolines and quinolines catalyzed by a Rh-thiourea chiral phosphine complex via anion binding", Chemical Science, vol. 7, Jan. 26, 2016, pp. 3047-3051.

Reena Rahi, et al., "Hydrogenation of quinolines, alkenes, and biodiesel by palladium nanoparticles supported on magnesium oxide", Dalton Transactions, vol. 41, Sep. 27, 2012, pp. 14490-14497.

Minfeng Fang, et al., "Ruthenium nanoparticles supported on magnesium oxide: A versatile and recyclable dual-site catalyst for hydrogenation of mono- and poly-cyclic arenes, N-heteroaromatics, and S-heteroaromatics", Journal of Catalysis, vol. 311, 2014, pp. 357-368.

Lei Zhang, et al., "Cooperation between the surface hydroxyl groups of Ru—$SiO_2$@$mSiO_2$ and water for good catalytic performance for hydrogenation of quinolone", Catalysis Science & Technology, vol. 4, Jan. 15, 2014, pp. 1939-1948.

Alena Karakulina, et al., "A Rhodium Nanoparticle—Lewis Acidic Ionic Liquid Catalyst for the Chemoselective Reduction of Heteroarenes", Angewandte Chemie International Edition, vol. 55, 2016, pp. 292-296.

* cited by examiner

Figure 3b [Figs. 3(b)-(3(d)]
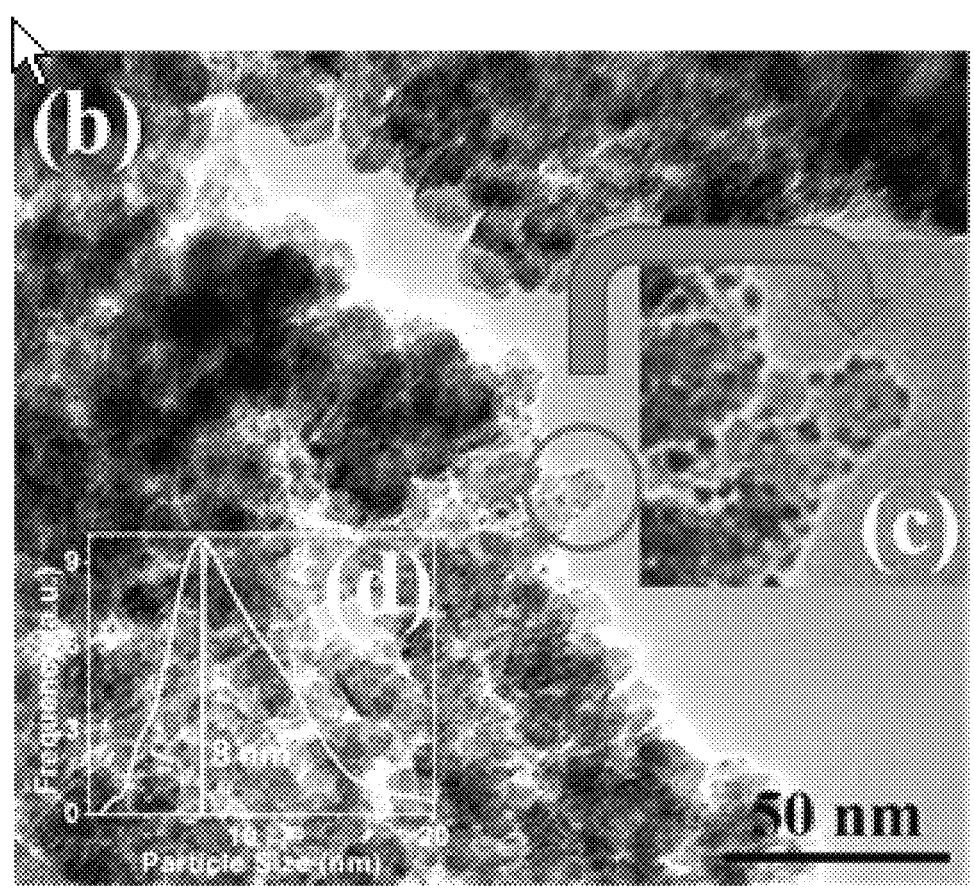

METHOD OF HYDROGENATING A COMPOUND HAVING AN N-HETEROCYCLIC AROMATIC RING

CROSS-REFERENCE TO RELATED APPLICATIONS

The present application is a Continuation of Ser. No. 16/366,586, now allowed, having a filing date of Mar. 27, 2019.

STATEMENT REGARDING PRIOR DISCLOSURE BY THE INVENTORS

Aspects of this technology are described in an article "Sub-nanometric Rh decorated magnetic nanoparticles as reusable catalysts for nitroarene reduction in water" published in Catalysis Communications, 2019, 119, 134-138, on Sep. 11, 2018, which is incorporated herein by reference in its entirety.

STATEMENT OF FUNDING ACKNOWLEDGEMENT

This project was funded by the Center of Research Excellence in Nanotechnology (CENT) of King Fahad University of Petroleum and Minerals (KFUPM), the Kingdom of Saudi Arabia; Award number NT-2018-MNS.

BACKGROUND OF THE INVENTION

Field of the Disclosure

The present invention relates to a method of catalytic reduction of carbocyclic and heterocyclic aromatic rings using a catalyst having subnano-particles of transition metal supported on superparamagnetic iron oxide nanoparticles (SPIONs).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Catalytic reduction of organic functional groups, such as alkene, alkyne, carbonyl, imine, and nitro is an important tool in organic synthesis (Minnaard et al. *Acc. Chem. Res.* 2007, 40, 1267-1277; Co et al. *Organometallics*, 2005, 24, 4824-4831; Farrar-Tobar et al. *Chem. Eur.* 1 2018, 24, 1-11; Sridharan et al. *Chem. Rev.* 2011, 111, 7157-7259; Zhou et al. *Angew. Chem. Int. Ed.* 2010, 49, 8121-81251; and Songl et al. *Appl. Catal. B*, 2018, 227, 386-408; each incorporated herein by reference in their entirety]. For example, reduction of N-heterocycle compounds, such as quinoline to 1,2,3,4-tetrahydroquinoline (bz-THQ) is of interest because bz-THQ is a building block for the synthesis of agrochemicals, pharmaceuticals, dyes, alkaloids and numerous other fine products [Sridharan et al. *Chem. Rev.* 2011, 111, 7157-7259, and Guthertz et al. *J. Am. Chem. Soc.* (2018), 140, 3156-3169 (DOI: 10.1021/jacs.8b00665)]. Heteroarene hydrogenation is challenging due to their relatively low reactivity and the presence of a pair of electrons on heteroatoms such as nitrogen which deactivates the catalysts (Rahi et al. *Dalton Trans.* 2012, 41, 14490-14497). Three reduction products of quinoline are possible which are 1,2,3,4-tetrahydroquinoline (bz-THQ), 5,6,7,8-tetrahydroquinoline (py-THQ), and decahydroquinoline (DHQ). Driving the reduction reaction to produce selectively one major product such as bz-THQ is challenging. Homogeneous catalysts of Ru, Rh, Ir and Pd have been used in the reduction of quinoline with good results (Guo et al. *Catal. Sci. Technol.*, 2017, 7, 2221-2228; Wang et al. *Chem. Rev.* 2012, 112, 2557-2590; Wen et al. *Chem. Sci.*, 2016, 7, 3047-3051; and Zhang et al. *Chem. Sci.*, 2016, 7, 4594-4599). For example, Fish and co-worker reported Rh-based catalyst ($\eta^5$-pentamethylcyclopentadienyl) rhodium dicationic complex, [Cp*Rh$(CH_3CN)_2]^{2+}$ for the regioselective reduction of nitrogen-containing model compounds such as quinoline (Konnerth et al. *Green Chem.*, 2017, 19, 2762-2767; Xia et al. *Catal. Sci. Technol.*, 2017, 7, 5515-5520; and Baralt et al. *J. Am. Chem. Soc.*, 1992, 114, 5187-5196). An iridium complex of BINOL-derived phosphoramidite PipPhos was used for the hydrogenation of a series of quinolones (Fish et al. *Organometallics*, 1991, 10, 54-56). Unfortunately, these homogeneous catalytic procedures suffer from serious drawbacks of employing harsh reaction conditions accompanied by a tedious and cumbersome purification process. The combination of low catalytic efficiency and restricted reusability was an impediment to wide use in industrial application.

Recent focus on the production of chemicals by environmentally friendly methods has required the development of recyclable and more efficient catalysts. Heterogeneous catalysis provides the advantage of easy separation of the catalyst from the reaction mixture and hence, the catalyst may be recycled (Fish et al. *J. Catal.* 1986, 102, 270-273; Mrsaic et al. *Adv. Synth. Catal.* 2008, 350, 1081-1089; and Wang et al. *J. Mater. Chem.*, 2009, 19, 8009-8014, each incorporated herein by reference in their entirety). Accordingly, numerous heterogeneous catalytic systems based on Ru, Rh, Ir, Pt, Pd and Au have been developed for the reduction of heterocylic compounds such as quinoline (Abu-Reziq et al. *J. Am. Chem. Soc.*, 2006, 128, 5279-5282; Polshettiwar et al. *Green Chem.*, 2010, 12, 743-754; Fang et al. *J. Catal.* 2014, 311, 357-368; Zhang et al. *Catal. Sci. Technol.* 2014, 4, 1939-1948; Zhu et al. *ChemCatChem* 2014, 6, 2954-2960; Wang et al. *Catal. Sci. Technol.* 2015, 5, 4746-4749; Karakulina et al. Angew. Chem. Int. Ed. 2016, 55, 292-296; Fan et al. *Catal. Commun.* 2013, 31, 81-85; Campanati et al. *J. Mol. Catal. A* 2002, 184, 267; Barbaro et al. *Green Chem.* 2012, 14, 3211-3219; Ge et al. *ChemCatChem* 2013, 5, 2183-2186; Gong et al. *J. Catal.* 2013, 297, 272-280; Dell'Anna et al. *Appl. Catal., A* 2014, 481, 89-95; and Mao et al. *Catal. Sci. Technol.* 2013, 3, 1612-1617). Although complete conversion of quinoline with good regioselectivity was observed at 50 bar or more of $H_2$ pressure and about 200° C. in some cases, the reaction progressed at a very slow rate. Also, the reaction involved the use of environmentally unfriendly and toxic organic solvents. Thus, there is a need for an alternative recyclable catalyst, where the reaction could be conducted at low temperature without employing hydrogen gas at high pressure in a green solvent such as water. To achieve such goals, judicious choice of a catalyst and a solid support would be required to obtain efficient regioselective reduction. Also, the catalyst should be separable from the reaction mixture and be reusable with relative ease. A number of precious metal-impregnated solid supports such as zeolite, polymer, silica, and cellulose have been investigated as catalytic systems [Fish et al.; Mrsaic et al.; Wang et al.; Abu-Reziq et al.; Polshettiwar et al.; Fang et al.; Zhang et al.; Zhu et al.;

Niu et al.; Karakulina et al.; Fan et al.; Campanati et al.; Barbaro et al.; Ge et al.; Gong et al.; Dell'Anna et al.; and Mao et al.]. However, a ligand-free metal supported on SPIONs has been rarely explored. It should be noted that solid-supported catalysts require post-reaction separation from the products. The separation is generally achieved by filtration, centrifugation, or precipitation, each of which severely affects the prospects of reusing the catalyst as a result of gradual loss of catalyst with each cycle [Tao et al. *Adv. Synth. Catal.* 2015, 357, 753-760].

Superparamagnetic iron oxide nanoparticles (SPIONs) have attracted a great deal of attention because they have desirable physical characteristics and are easily obtainable from low cost precursors. They are insoluble in water and other common solvents, and have magnetic characteristics that render their separation from reaction mixtures by an external magnet effortless. Magnetically separable catalysts have been utilized in the syntheses of biphenyl and higher olefins, and in the asymmetric hydrogenation of ketones and transesterification of triglycerides to produce biodiesel [Yan et al. *Org. Lett.* 2013, 15, 1484-1487; McDonald et al. *Green Chem.*, 2008, 10, 424-432; Wang et al. *Tetrahedron Lett.*, 2013, 54, 238-241; and Zhu et al. *Adv. Synth. Catal.*, 2007, 349, 1917-1922].

U.S. Pat. No. 9,480,978B1 discloses a catalyst comprising iron oxide ($Fe_2O_4$) nanoparticle core and bis(diarylphosphinomethyl dopamine anchored on the surface as a ligand to a metal catalyst. Also, it discloses that the metal catalyst is selected from nickel, platinum, palladium, rhodium, iron, gold, silver, ruthenium, and iridium. In particular, the patent discloses that the metal catalyst is rhodium(III) chloride or 2,5-norbornadiene-rhodium (I) chloride. The patent further discloses the use of the coordinated rhodium catalyst in hydroformylating an olefin to the corresponding aldehyde.

Pelisson et al. [*ACS Sustainable Chem. Eng.* (2016) 4, 3, 1834-1839] disclose the preparation of $Rh°/\gamma Fe_2O_3$ nanocomposite by depositing metal nanoparticles on non-functionalized magnetic support through a wet impregnation method. The nanocomposite is shown to be an effective catalyst at room temperature for hydrogenation of nitrobenzene to aniline and dechlorination of chloroarene compounds and can be magnetically retrieved from reaction mixtures Laska et al. [Catal. Letters (2008) 122 (1-2), 68-75] disclose rhodium catalyst supported on SPIONs prepared by a method involving sulfonated triphenylphosphoine ligands. The catalyst promoted the hydrogenation of olefins and the addition of arylboronic acids to dimethyl itaconate in water.

Accordingly one object of the present disclosure is to provide a regioselective reduction method for aromatic compounds in general and aromatic heterocyclic compounds in particular using an efficient and recyclable catalyst that can be removed from a reaction mixture by a magnet.

SUMMARY

A first aspect of the invention is directed to a method of hydrogenating an aromatic ring in a compound comprising:
  suspending a catalyst in a solvent to form a catalyst mixture, wherein the catalyst consists of superparamagnetic iron oxide nanoparticles (SPIONs) and transition metal particles of less than 1 nm deposited on the superparamagnetic iron oxide nanoparticles,
  mixing the catalyst mixture with a compound comprising an aromatic ring and a reducing agent, and
  heating to a temperature in the range of 40 to 200° C.

In a preferred embodiment, the transition metal is selected from rhodium (Rh), platinum (Pt), palladium (Pd), ruthenium (Ru), nickel (Ni), copper (Cu), osmium (Os), iridium (Ir), rhenium (Re), gold (Au), and silver (Ag).

In another preferred embodiment, the aromatic ring is heterocyclic ring or a carbocyclic ring.

In a more preferred embodiment, the aromatic ring is a nitrogen heterocyclic ring.

In the most preferred embodiment, the nitrogen heterocyclic ring is a five membered ring or six membered ring.

In another preferred embodiment, the nitrogen heterocyclic ring is in a compound selected from the group consisting of optionally substituted or unsubstituted pyrrole, pyridine, pyrazol, imidazole, triazol, tetrazol, indole, quinoline, isoquinoline, pyrimidine, pyridazine, pyrazine, purine, oxazol, thiazol, isothiazol, 1,2-oxazine, 1,3-oxazine, 1,4-oxazine, 1,2-thiazine, 1,3-thiazine, 1,4-thiazine, 1,2,3-triazine, 1,2,4-triazine, and 1,3,5-triazine.

In another preferred embodiment the aromatic ring is carbocyclic ring.

In another preferred embodiment, the carbocyclic aromatic ring is a in a compound selected from the group consisting of optionally substituted or unsubstituted benzene, biphenyl, naphthalene, anthracene, pyrene, benz[a]anthracene, benzo[a]pyrene, or the like.

In a more preferred embodiment, the compound is selected from optionally substituted or unsubstituted benzene, toluene, and xylene.

In another preferred embodiment, the reducing reagent is hydrogen gas, tetrahydroxydiboron (THDB), sodium borohydride, lithium borohydride, lithium aluminum hydride, diborane, calcium hydride, sodium hydride, potassium hydride, or disobutylaluminum hydride.

In another preferred embodiment, the reducing reagent is THDB.

In another preferred embodiment, the reducing reagent is pressurized hydrogen gas in the range of 2 bar to 100 bar.

In another preferred embodiment the solvent is a compound containing the aromatic ring.

In another preferred embodiment, the solvent is water, an alcohol, a carbocyclic aromatic solvent, a polar aprotic polar solvent or a mixture thereof.

In another preferred embodiment, the solvent is an alcohol selected from methanol, ethanol, propanol, isopropanol, butanol, isobutanol, t-butyl alcohol, dimethyl ether, diethyl ether, and the like In another preferred embodiment, the polar aprotic polar aprotic solvent is selected form tetrahydrofurane, dioxane, dimethylformamide, acetonitrile, dimethylacetamide, and the like.

In another preferred embodiment, the method comprises:
  suspending a catalyst in a solvent selected from the group consisting of water, methanol, ethanol, propanol, isopropanol, butanol, a compound comprising the N-heterocyclic ring, and a mixture thereof to form a catalyst mixture, wherein the catalyst consists of superparamagnetic iron oxide nanoparticles (SPIONs) and rhodium particle of less than 1 nm deposited on the SPIONs,
  mixing the catalyst mixture with a compound comprising an N-heterocylcic aromatic ring and tetrahydroxydiboron (THDB), and
  heating to a temperature in the range of 40 to 100° C.

In a more preferred embodiment, the solvent is water.

In another preferred embodiment, the N-aromatic heterocycle is selected from pyrrole, pyridine, pyrazol, imidazole, triazol, tetrazol, indole, quinoline, isoquinoline, pyrimidine, pyridazine, pyrazine, purine, oxazol, thiazol, isothiazol, 1,2- oxazine, 1,3-oxazine, 1,4-oxazine, 1,2-thiazine, 1,3-thiazine, 1,4-thiazine, 1,2,3-triazine, 1,2,4-triazine, and 1,3,5-triazine.

In another preferred embodiment, the method comprises:
  suspending a catalyst in a solvent selected from the group consisting of water, methanol, ethanol, propanol, isopropanol, butanol, a compound comprising the carbocyclic aromatic ring, and a mixture thereof to form a catalyst mixture, wherein the catalyst consists of superparamagnetic iron oxide nanoparticles (SPIONs) and rhodium particle of less than 1 nm deposited on the SPIONs,
  mixing the catalyst mixture with a compound comprising a carbocyclic aromatic ring and hydrogen gas at a pressure in the range of 2 bar to 100 bar, and
  heating to a temperature in the range of 40 to 100° C.

In another preferred embodiment, the solvent is the aromatic compound.

In another preferred embodiment, the aromatic compound is selected from benzene, toluene, and xylene.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3b shows TEM images of Rh@$Fe_3O_4$. Insets FIG. 3c shows magnified image of Rh nanoparticles decorating the $Fe_3O_4$ particles. Inset, FIG. 3d shows particle size distribution curve of Rh@$Fe_3O_4$, and circled STEM image of Rh@$Fe_3O_4$ particles shows Rh nanoparticle with a size: ~<1 nm.

DETAILED DESCRIPTION

Figure 1:
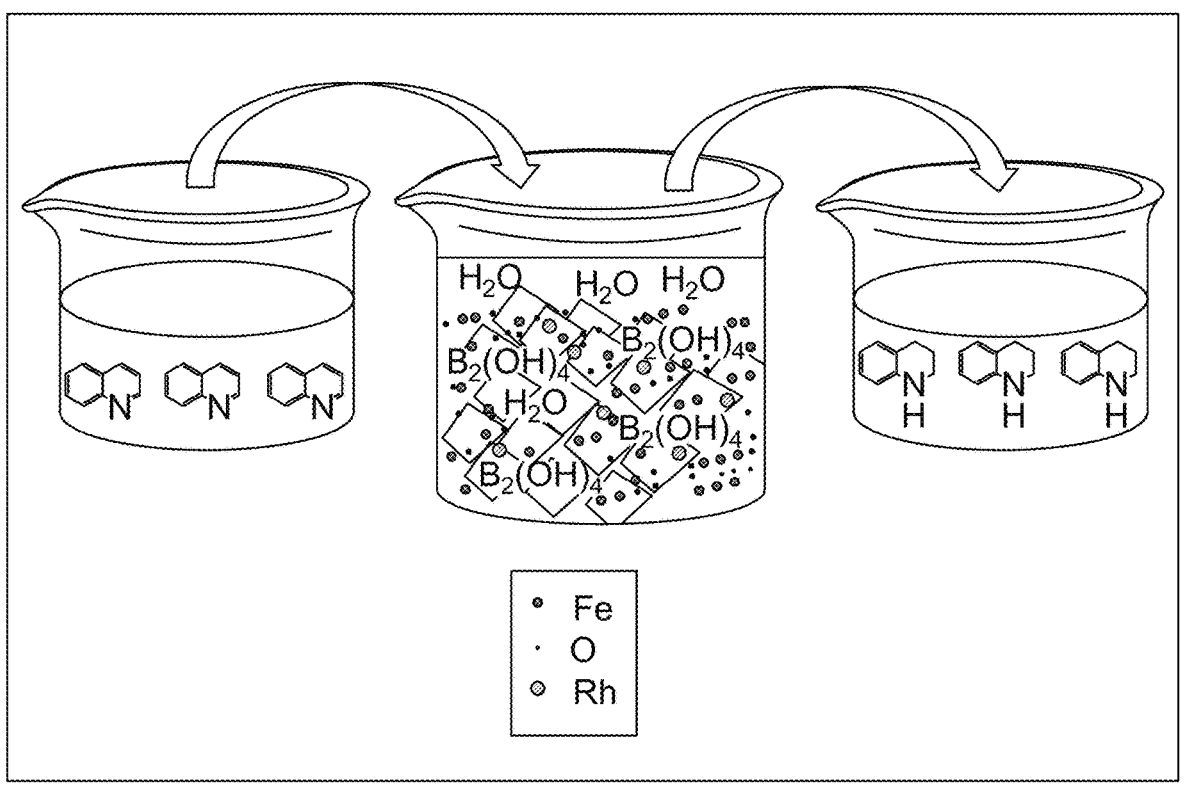
FIG. 1 shows pictorial representation of quinoline hydrogenation using catalyst, Rh@$Fe_3O_4$, and THDB as hydrogen source in water.

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the term "compound" is intended to refer to a chemical entity, whether in a solid, liquid or gaseous phase, and whether in a crude mixture or purified and isolated.

As used herein, the term "salt" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein, the term "alkyl" unless otherwise specified refers to both branched and straight chain saturated aliphatic primary, secondary, and/or tertiary hydrocarbons of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, alkoxy, aryloxy, or combination thereof.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylation, arylthio, aryl alkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, naphthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

As used herein, the term "alcohol" unless otherwise specified refers to a chemical compound having an alkyl group bonded to a hydroxyl group. Many alcohols are known in the art including, but not limited to, methanol, ethanol, propanol, isopropanol, butanol, isobutanol and t-butanol, as well as pentanol, hexanol, heptanol and isomers thereof. Since the alkyl group may be substituted with one or more hydroxyl group, the term "alcohol" includes diols, triol, and sugar alcohols such as, but not limited to, ethylene glycol, propylene glycol, glycerol, and polyol.

As used herein the terms "reduction" and "reducing agent" have the well accepted meaning in the chemical art. So a reducing agent causes the reduction of an organic compound by decreasing its oxidation state. For example, the addition of hydrogen atoms to aromatic ring by a reducing agent is a reduction reaction.

The disclosure is directed to a method of hydrogenating an aromatic ring in a compound comprising:
  suspending a catalyst in a solvent to form a catalyst mixture, wherein the catalyst consists of superparamagnetic iron oxide nanoparticles (SPIONs) and transition metal particles of less than 1 nm deposited on the superparamagnetic iron oxide nanoparticles,
  mixing the catalyst mixture with a compound comprising an aromatic ring and a reducing agent, and
  heating to a temperature in the range of 40 to 200° C.

The catalyst of the invention contains and preferably consists of transition metal particles having a diameter of less than 1 nm, preferably less 0.8 nm, more preferably less than 0.7 nm, and most preferably about 0.5 nm deposited on superparamagnetic iron oxide nanoparticles (SPIONs). The SPIONs are iron oxide (Fe$_2$O$_4$) nanoparticles having an average diameter in the range of 3 nm to 100 nm, preferably in the range 4 nm to 50 nm, more preferably in the range of 5 to 25 nm, and most preferably in the range of 6 nm to 15 nm. In a particularly preferred embodiment the SPIONs have an average diameter in the range 7 nm to 10 nm. In one or more embodiments, the transition metal is present in an amount in the range of 1-20 wt. %, preferably in the range of 3-15 wt. %, more preferably in the range of 4-10 wt. % relative to a total weight of the supported catalyst. For example, the rhodium is present in an amount of about 4.2 wt. %, about 6.5 wt. %, or about 8.2 wt. % relative to a total weight of the supported catalyst. In a most preferred embodiment, the transition is present in an amount of about 8.2 wt. % relative to a total weight of the supported catalyst, and metal particles are dispersed on the surface of the SPIONs. The transition metal of the catalyst may be any transition metal that is able to catalyze the reduction reaction of an aromatic and/or heteroaromatic ring. Examples of transition metals useful as catalysts include, but are not limited to, rhodium, platinum (Pt), palladium (Pd), ruthenium (Ru), nickel (Ni), copper (Cu), osmium (Os), iridium (Ir), rhenium (Re), gold (Au), silver (Ag) and mixtures or alloys thereof. In a particularly preferred embodiment, the transition metal is rhodium.

The aromatic compound to be reduced can be any compound comprising an aromatic ring. In some embodiments, the aromatic compound is an optionally substituted heterocyclic compound. As used herein the term "aromatic heterocyclic compound" has the established meaning in the chemical art and is intended to refer to an aromatic compound comprising a heterocyclic aromatic ring. The heterocyclic ring has one or more heteroatom. The heteroatoms include are but not limited to, nitrogen, oxygen, sulfur, or combination thereof. Examples of nitrogen containing heterocyclic aromatic compounds include, but are not limited to, pyrol, imidazole, pyrazol, triazol, tetrazol, pyridine, pyrazine, pyrimidine, purine, quinoline, quinolin2(1H)-one, isoquinoline, isoquinolin-1(2H)-one, phathalazine, quinazoline, cinnoline, quinoxaline, carbazol, 1,8-naphtharidine, pyrido[3,2-d]pyrimidine, acridine, phenazine, phenoxazine and the like. Examples of oxygen containing heterocyclic aromatic compounds include, but are not limited to, furan, benzofuran, 2-pyrone, 4-pyrone, coumarin, 7-methoxycumarin, chromone, and dibenzofurane. Examples of sulfur containing heterocyclic aromatic compounds include, but are not limited to, thiophen, benzothiophene, and dibenzothiophene. Examples of heterocyclic compounds comprising a combination of hetero atoms include, but are not limited to, thiazol, oxazol, isoxazole, isothiazol, 1,2,5-oxadiazole, phenoxazine, phenothiazine, and phinoxathiin.

In some preferred embodiment, the heterocyclic aromatic compound may be substituted with a substituents which may be reduced along with the heteraromatic ring. Such a substituents include, but not limited to nitro, chloro, and iodo substituent. For example, the nitro group is reduced to amino group and the chloro substituent is replaced by a hydrogen.

In some more preferred embodiments of the method, a heterocyclic aromatic ring may be regioselectively reduced in a heterocyclic compound comprising a carbocyclic aromatic ring under relatively mild condition in aqueous solution. For example, quinoline and isoquinoline are reduced regiospecifically to 1,2,3,4-tetrahydroquinoline and 1,2,3,4-tetrahydroisoquinoline, respectively, in aqueous medium.

In other preferred embodiments, the aromatic compound is an optionally substituted carbocyclic aromatic compound such as but not limited to benzene, naphthalene, anthracene, phenanthrene, pyrene, benz[a]anthracene, benzo[a]pyrene, and the like. There are large numbers of substituted carbocyclic aromatic compounds known in the art. For example, substituted benzene compounds such as, but not limited to toluene, o-xylene, m-xylene, p-xylene, anisol, phenol, hydroxyanisol isomers, dihydroxyphenol isomers, trihydroxybenzene, polyphenols, halogenated benzene such as chlorobenzene, dichlorobenzene and isomers thereof, bromobenzene, dibromobenzene and isomers thereof, tribromobenzene and isomers thereof, fluorinated benzene, and iodinated benzene can be reduced by the method of invention. Other well-known substituted carbocyclic aromatic compounds include, but not limited to methylated, hydroxylated, and halogenated naphthalene, methylated, hydroxylated, and halogenated anthracene, methylated, hydroxylated, and halogenated phenanthrene, methylated, hydroxylated, and halogenated benz[a]anthracene, and methylated, hydroxylated, and halogenated pyrene and benzo[a]pyrene.

In some preferred embodiment, the carbocyclic aromatic compound may be substituted with a substituents which may be reduced along with the carbocyclic aromatic ring. Such a substituents include, but not limited to nitro, chloro, and iodo substituent. For example, the hydrogenation of nitrobenzene would produce cyclohexyl amine and chlorobenzene would produce hexane.

Any reducing agent may be utilized with the catalyst of the invention in the reduction method. Example of reducing agents suitable to use with the catalyst of the invention include, but not limited to hydrogen gas, sodium borohydride, lithium borohydride, lithium aluminum hydride, tetrahydroxydiboron, diborane, calcium hydride, sodium hydride, potassium hydride, disobutylaluminum hydride, and combination thereof.

Any liquid may be utilized as a solvent in the method of the invention including the aromatic compound to be reduced. Examples of the solvent to be used in the method include, but are not limited to water, alcohol such as, but not limited to, methanol, ethanol, propanol, isopropanol, 1-butanol and isomers thereof, ethers such as, but not limited to, dimethyl ether, diethyl ether, methylethyl ether, dimethyl formamide, tetrahydrofurane, dioxane, benzene, toluene, xylenes, hexane, cyclopentane, hexane, cyclohexane, and the like. Since some reducing agents may react violently with water and alcohols, care should be taken in selecting the combination of a solvent and a reducing agent so that the solvent does not inactivate the reducing agent. For example hydrogen gas or tetrahydroxydiborn may be utilized in a method using any solvent, whereas lithium aluminum hydride or diborane would be used with non-polar or polar aprotic solvents such as dioxane, tetrahydrofurane, benzene and toluene.

The use of hydrogen gas as a reducing agent in the method of the invention may require pressurizing the hydrogen gas at a pressure in the range 1 to 200 bars, preferably in the range 5 to 100 bars, more preferably in the range of 10 to 75 bars, and most preferably in the range of 15 to 50 bars.

In some preferred embodiments, the molar ratio of aromatic compound to reducing agent is in the range of 1 to 50, preferably in the range 2 to 25, more preferably in the range 3 to 25, and most preferably in the range of 4 to 10.

Since the catalytic reduction method of the invention is sensitive to solvent used in the method and the reactivity of the aromatic compound to reduction, the temperature of the reaction may be set to produce the desired product in a reasonable amount of time. One of ordinary skill in the art would be able to determine the appropriate temperature and the reasonable time for the reaction of interest. In some embodiments, the reaction temperature is in the range of 40 to 80° C., whereas in some other embodiments the reaction temperature is in the range of 80 to 200° C.

The examples below are intended to further illustrate protocols for preparing, characterizing transition metal supported SPIONs, and uses thereof, and are not intended to limit the scope of the claims.

Example 1

Materials:

All chemicals were purchased from Sigma-Aldrich and were used without further purification unless otherwise indicated. Standard procedures were followed for drying and deoxygenating solvents. Schlenk line techniques were used to carry out reactions under inert atmosphere wherever needed. Deionized (DI) water (specific conductivity: 18.2 mΩ) was used in all the experiments.

Methods:

Fourier-Transform Infrared (FTIR) spectroscopic data were obtained on a Nicolet 720 in the wave number range of 400 to 4000 $cm^{-1}$ using KBr as the IR transparent window material. X-ray diffraction data were collected on Rigaku model Ultima-IV diffractometer employing Cu—$K_\alpha$ radiation (X, =1.5405 Å) at 40 kV and 25 mA over a 2θ range between 20 and 90°. The Transmission Electron Microscopy images were acquired at the Instituto de Nanociencia de Aragon (LMA-INA), University of Zaragoza, Spain, on a TEM (Joel, J E M 2011) operated at 200 kV with 4 k×4 k CCD camera (Ultra Scan 400SP, Gatan). The TEM samples were prepared by dropping on a copper grid from an ethanolic suspension and drying at room temperature. The amount of Rh in the catalyst was determined by Inductively Coupled Optical Emission Spectrometry (ICP-OES; PlasmaQuant PO 9000-Analytik Jena). The samples were dissolved in a dilute $HNO_3$ and HCl mixture. Calibration curves were prepared for Rh and Fe using standard solutions (ICP Element Standard solutions, Merk). Samples for Scanning Electron Microscopy (SEM) were prepared from ethanolic suspensions on alumina stubs and coated with gold in an automatic gold coater (Quorum, Q150T E). For the elemental analysis and mapping, the energy dispersive X-ray spectra (EDS) were collected on a Lyra 3 attachment to the SEM. The magnetic susceptibilities were measured at room temperature using a vibrating sample magnetometer (VSM, model PMC Micromag 3900) equipped with a 1 tesla magnet. Catalytic reactions were performed in Teflon lined autoclaves from HiTech, USA (model M010SSG0010-E129A-00022-1D1101), fitted with a pressure gauge and a mechanical stirrer. Catalytic products were identified by a Shimadzu 2010 Plus (Japan) gas chromatograph equipped with a mass spectrometer. The disappearance of the reactant and sequential appearance of the product was recorded in real-time, identifying the species in terms of their molecular ion ($M^+$) by comparing and matching them with the available Willey library of the mass spectrum database, in addition to the identification of mass fragmentation. Solution $^1$H and $^{13}$C NMR experiments were performed on a Bruker Ascend 400 spectrometer at Saudi International Petrochemical Company (SIPCHEM) in Dhahran Techno Valley (DTV) and chemical shifts (δ) values were referenced to tetramethylsilane (TMS) as an internal standard.

Example 2

Synthesis of Rh@Fe$_3$O$_4$ Catalyst:

The catalyst was prepared as described in a co-pending application Ser. No. 16/359,409 titled "[An Iron Oxide Supported Rhodium Catalyst for Nitroarene Reduction]") which is incorporated herein by reference in its entirety. Magnetite (Fe$_3$O$_4$) nanoparticles in the range of 7-9 nm were prepared according to a procedure described elsewhere [Panella et al. *J. Catal.*, 2009, 261, 88-93; and Tang et al. *Fuel Process. Technol.*, 2012, 95, 84-89—each incorporated herein by reference in its entirety]. In a typical preparation, nanostructured magnetite was prepared from an alkaline solution containing Fe(II) and Fe(III) precursors in the molar ratio of 1:2. The black powder (200 mg) was suspended in ethanol, sonicated for 3 h. An aqueous solution containing 0.019 g of Rh(NO$_3$)$_3$ (0.19 mmol was added and the mixture stirred overnight. The mixture was heated to 50° C. for 3 h, and 27 M ammonium hydroxide solution was slowly added to pH >12 with continued stirring for additional 4 h to insure uniform dispersion of the catalytic species on the magnetic support. The resulting black solid was precipitated and separated by placing a magnet at the bottom of the flask, and washed with several aliquots of DI water (5×30 mL) and finally with ethanol.

Example 3

Quinoline Reduction with THDB:

The catalytic reduction of quinoline was performed in a parallel 10-place reaction tube reactor fitted with a magnetic stirrer and a Teflon stopper. To a suspension of 2.0 mg Rh@Fe$_3$O$_4$ in 2 mL DI water, quinoline (0.5 mmol, 0.65 μL) was added and the system flushed with N$_2$ gas 3 times. Tetrahydroxydiboron (THDB, 4 mmol) was added. The tube was capped tightly with Teflon stopper and heated at 80° C. The reaction progress was monitored by TLC (thin layer chromatography). The product was extracted from the aqueous medium with ethyl acetate and the ethyl acetate solution dried with sodium sulfate and the solvent evaporated under reduced pressure. The residue containing the product was eluted from a short silica gel column using a mixture of ethyl acetate and hexane (8:2). Conversion was measured by GC and identified by the GC-MS.

Example 4

Aromatic Compounds Reduction with Hydrogen Gas:

Rh@Fe$_3$O$_4$ catalyst (5 mg) and the selected reactant (for example, pyridine, 0.5 mL) mixture was placed in a Teflon-lined autoclave fitted with a pressure gauge, mechanical stirring and automatic temperature controller. The reactor was flushed repeatedly with H$_2$, filled with H$_2$ up to 40 bars, and the reaction initiated with heating and stirring and continued for 10 h. Then, the reactor was allowed to cool down to room temperature, depressurized, and opened. The degree of conversion was determined by GC and the product was identified by the NMR or GC-MS.

Similar methods were used for the hydrogenation of aromatic hydrocarbons such as benzene, toluene and xylene.

Example 5

Figure 2:
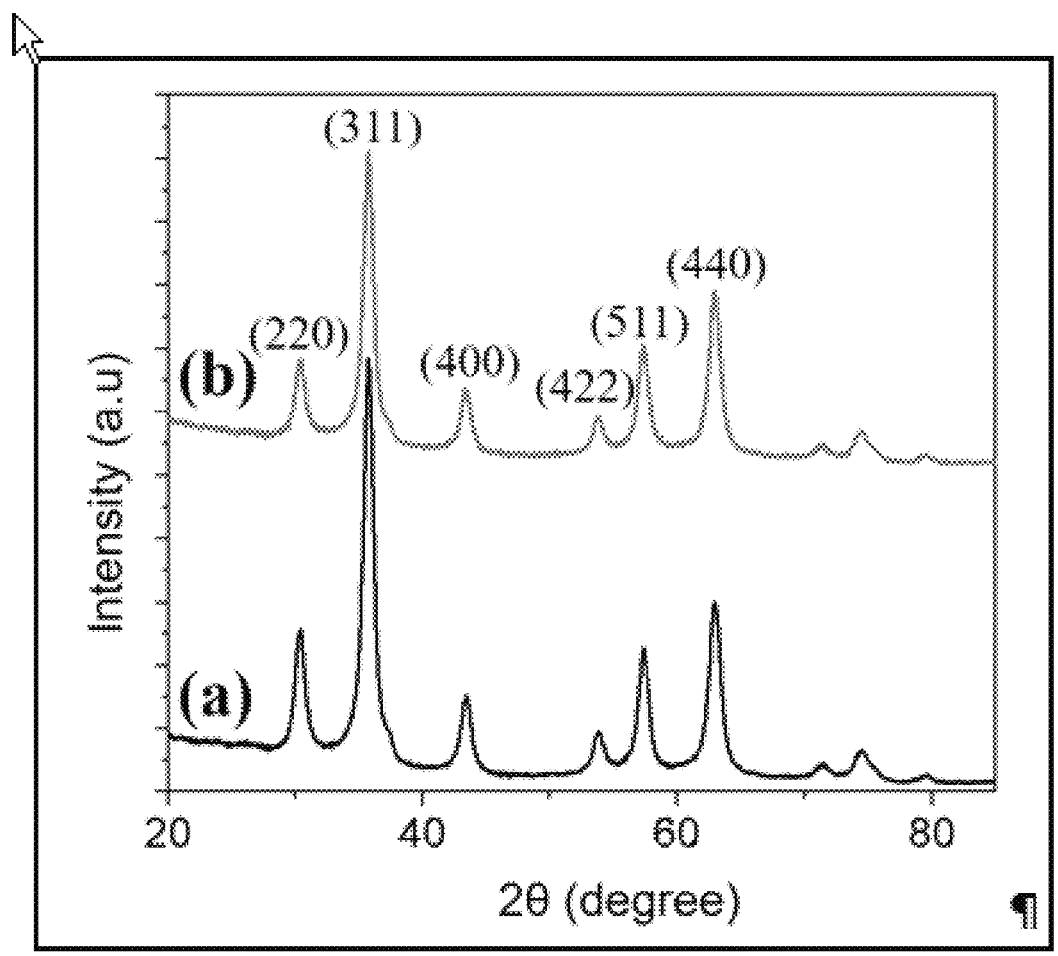
FIG. 2 shows XRD spectra of a) $Fe_3O_4$ and b) Rh@$Fe_3O_4$.
Figure 5A:
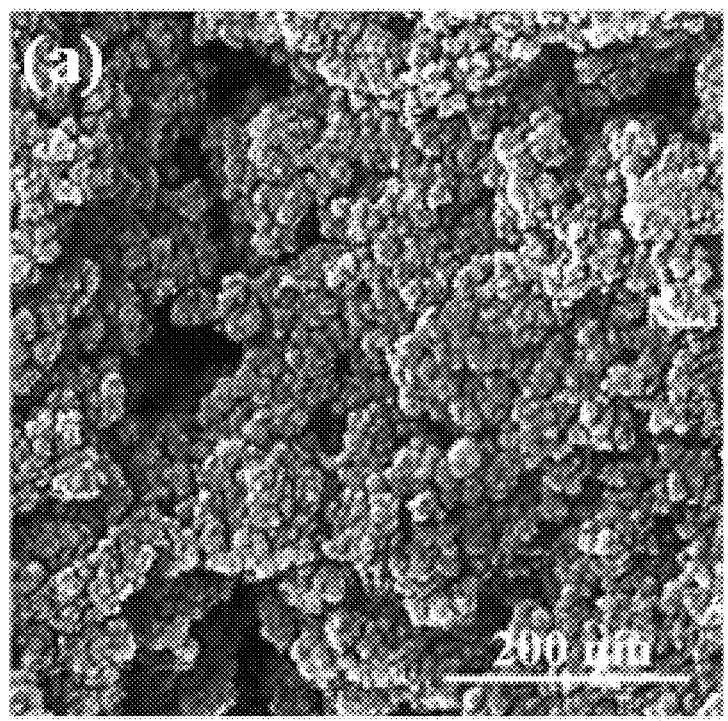
FIG. 5a shows SEM image of $Fe_3O_4$.
Figure 5B:
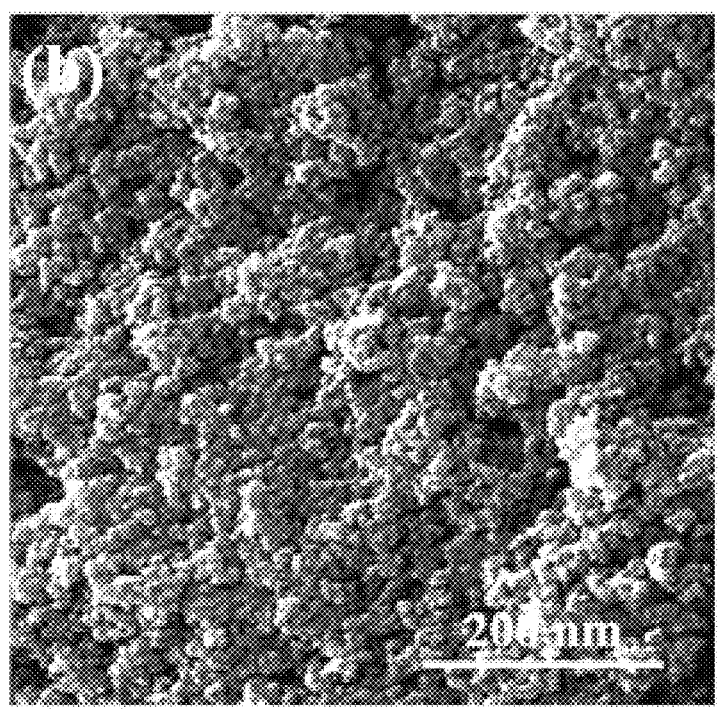
FIG. 5b shows SEM image of Rh@$Fe_3O_4$.

Structure Characterization of the Catalyst:

Structural characterization of the catalyst was carried out by a number of analytical and spectroscopic techniques. The phase analysis was investigated by X-ray diffraction. FIG. 2 shows the XRD signature of magnetite with Rh line (a) and without Rh line (b). High crystallinity of the freshly prepared Rh@F$_3$O$_4$ is evident from the diffraction pattern, which corresponds to that of magnetite spinel structure and superimposition with the pure Fe$_3$O$_4$ peaks indicates the preservation of Fe$_3$O$_4$ structural lattice arrangement upon decoration of sub-nanosized Rh particles. XRD angle at (2θ) 30.22°, 35.70°, 43.10°, 53.40°, 57.10° and 63.20° demonstrated the purity and formation of single phase nanomaterials with cubic structure (JCPDS card No. 01-075-0449) of magnetite (Fe$_3$O$_4$) [Shaikh et al. *New J. Chem.*, 2015, 39, 7293-7299]. It is noteworthy that there was no observed recognizable peak(s) of Rh in the diffraction pattern, probably due to the low concentration of Rh and the sub-nanometer particle size of Rh. The size of magnetite crystallites was estimated to be less than 10 nm from Debye-Scherrer equation; which was validated from the FESEM (See FIGS. 5a and 5b) and TEM images of the catalyst specimen (FIGS. 3a to 3g). The structural refinement performed by using the Rietveld method (see Table 1) which confirmed the formation of the desired phase in high purity with a goodness of fit close to the unity (GoF=1.07-1.13). This suggests that incorporation of Rh particles did not alter the structure nor dilate the lattice of the parent support, suggesting that SPIONs remained stable during the Rh particles decoration process.

TABLE 1

Structure and microstructural parameters obtained by Rietveld refinements.

| Material | Phase (%) | Crystallite size (nm) | Micro-strain (%) | Space group | Lattice parameter (a = b = c) (Å) | GoF |
|---|---|---|---|---|---|---|
| Fe$_3$O$_4$ | 100 | 8.24 | 0.68 | Fd-3m (227) | 8.349 | 1.13 |
| Rh @ Fe$_3$O$_4$ | 100 | 8.40 | 0.54 | Fd-3m (227) | 8.362 | 1.08 |

Figure 3A:
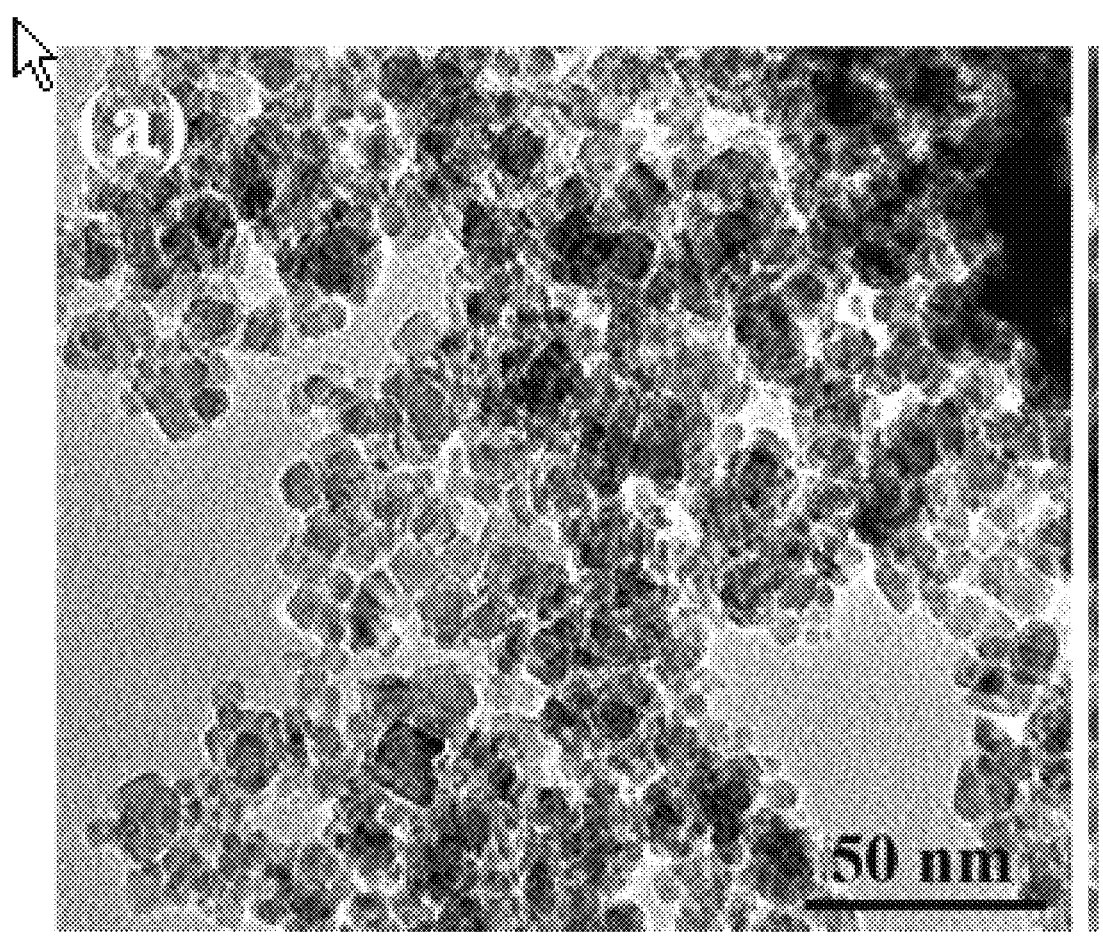
FIG. 3a shows TEM images of $Fe_3O_4$.
Figure 3E:
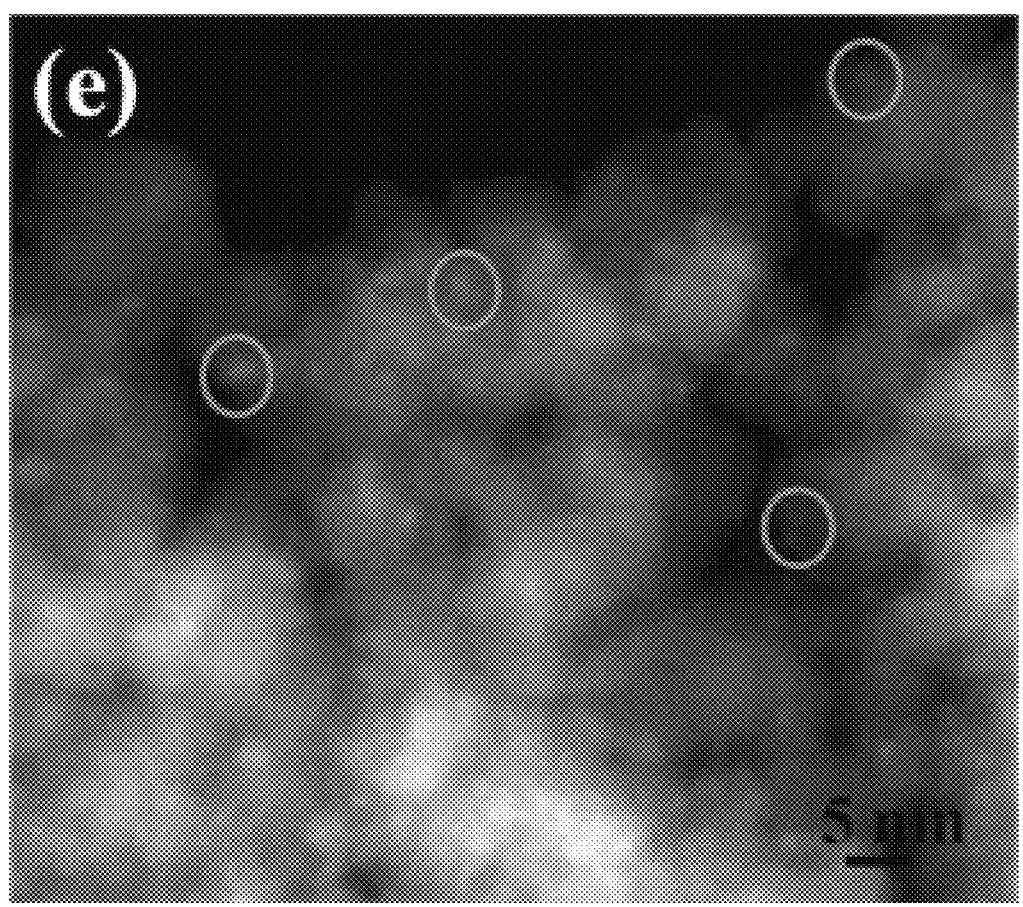
FIG. 3e shows HRTEM image of Rh@$Fe_3O_4$.
Figures 3F, 3G:
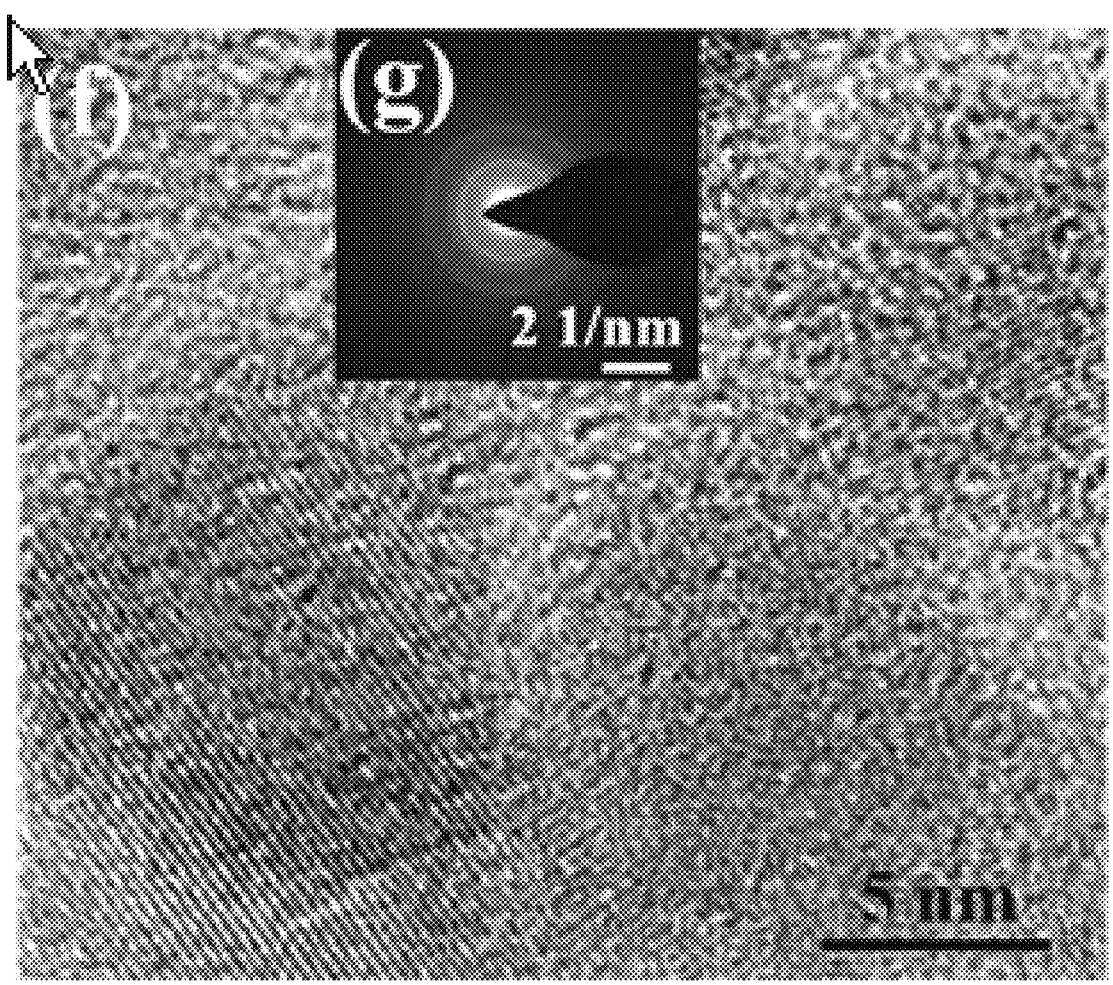
FIG. 3F show a TEM image Rh@$Fe_3O_4$; inset 3 g shows the selected area electron diffraction (SAED) pattern of $Fe_3O_4$ from Rh@$Fe_3O_4$.
Figure 6A:
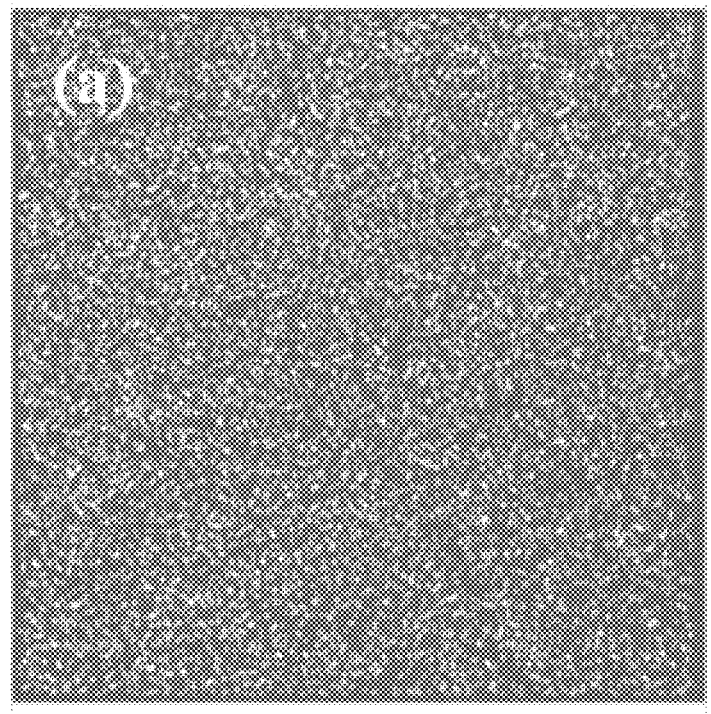
FIG. 6a shows Fe mapping of Rh@$Fe_3O_4$.
Figure 6B:
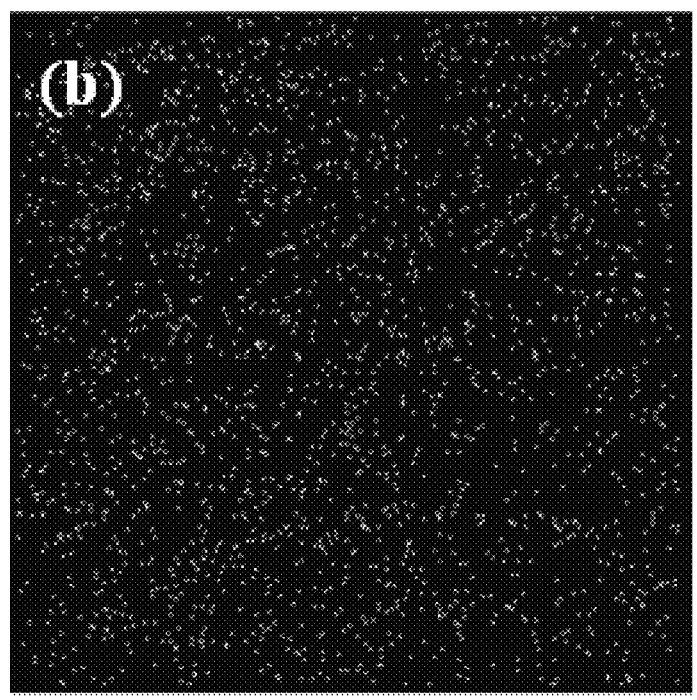
FIG. 6b shows Rh mapping of Rh@$Fe_3O_4$.
Figure 7:
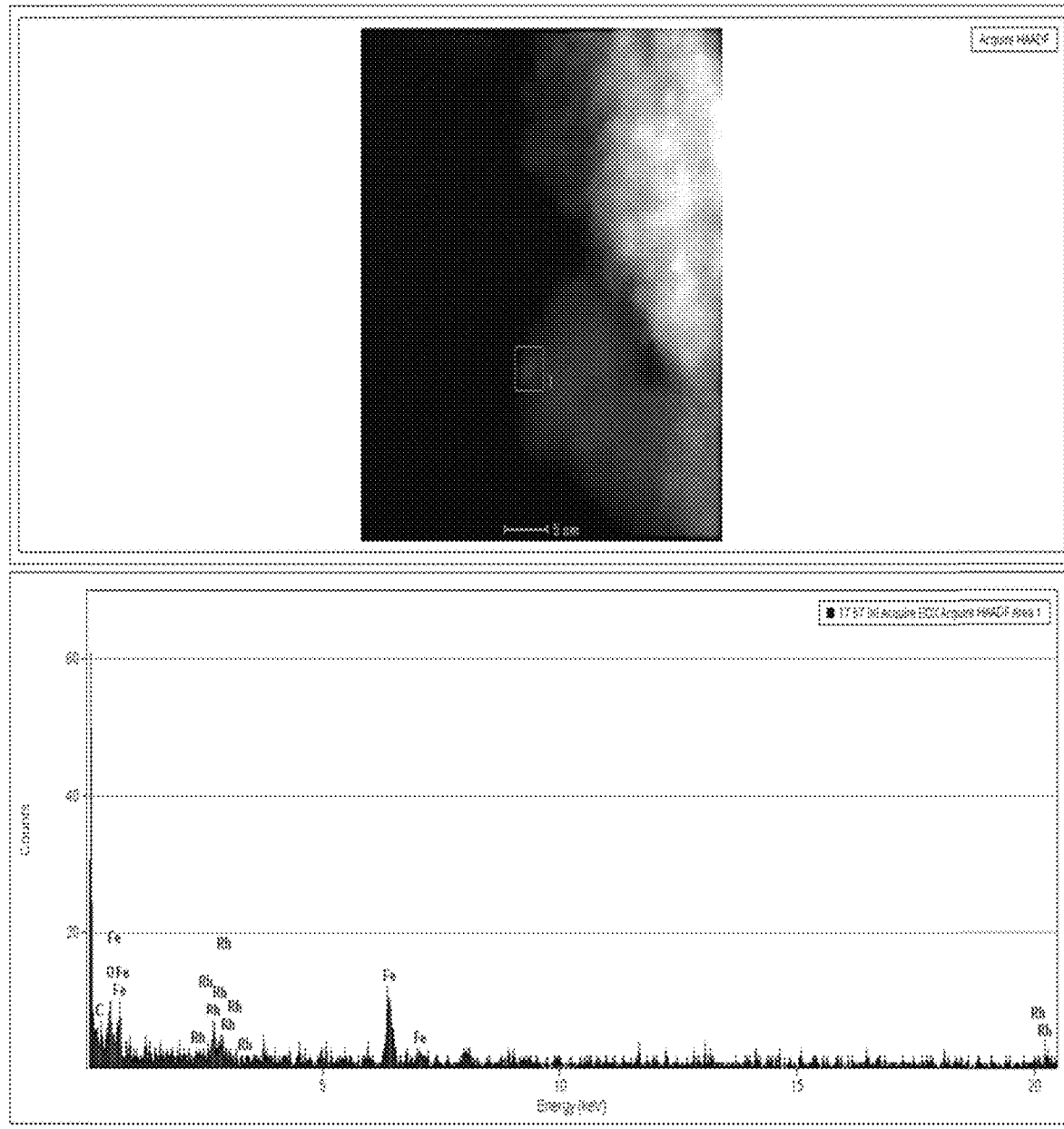
FIG. 7 shows STEM image of Rh@$Fe_3O_4$ (top) and elemental identification of Rh.
Figure 8:
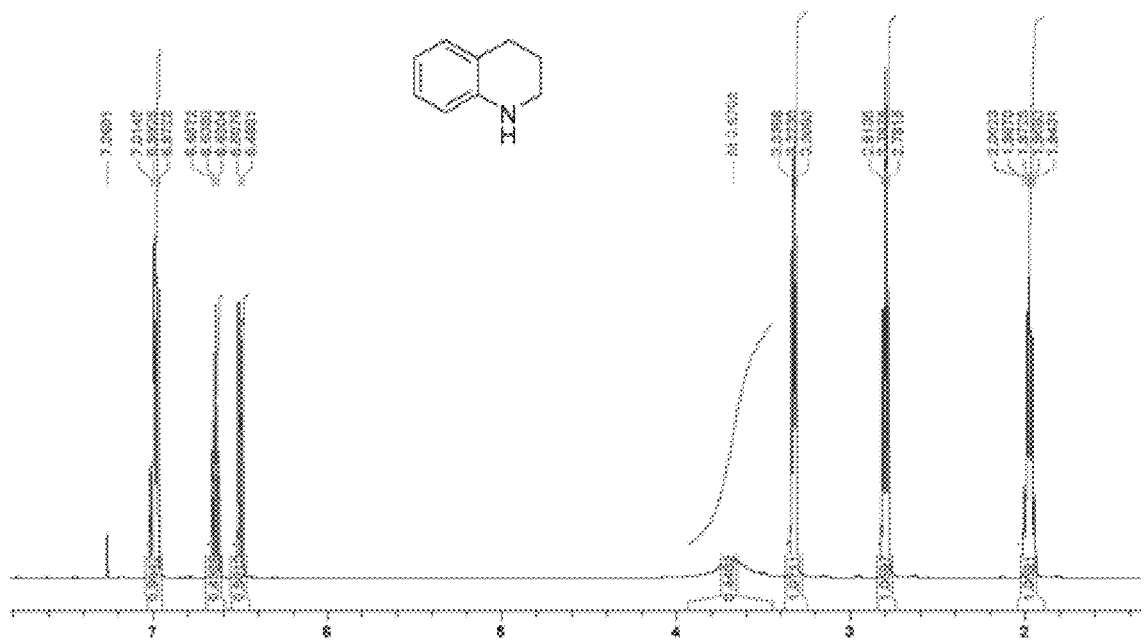
FIG. 8 shows $^1H$ NMR of Bz-THQ obtained from the Quinoline hydrogenation in water.
Figure 9:
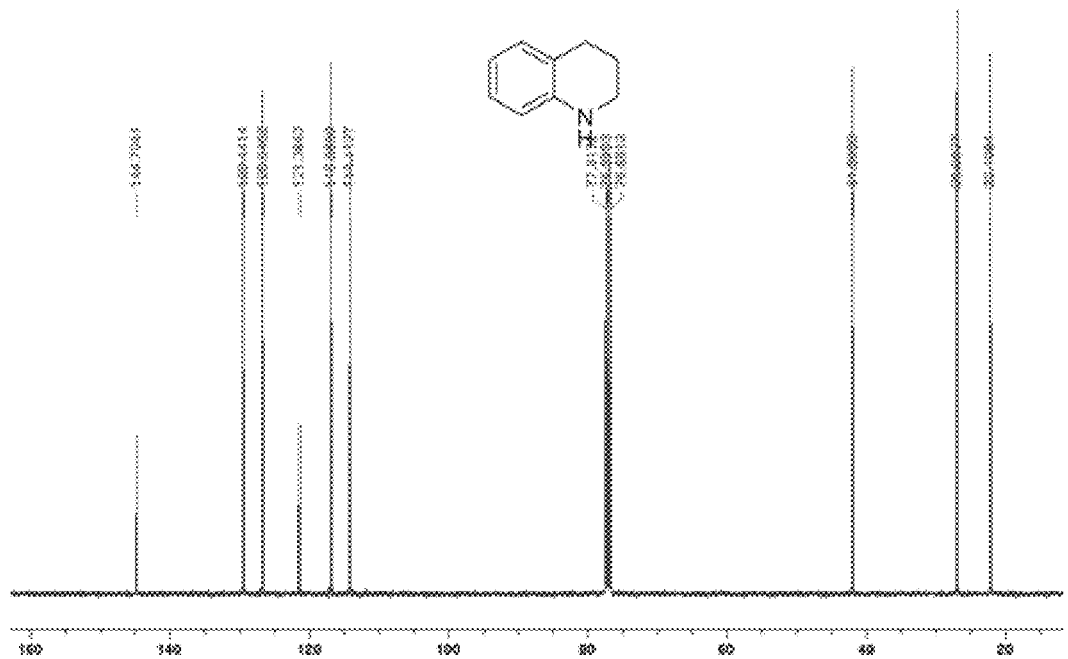
FIG. 9 shows $^{13}C$ NMR of Bz-THQ obtained from the Quinoline hydrogenation in water.
Figure 10:
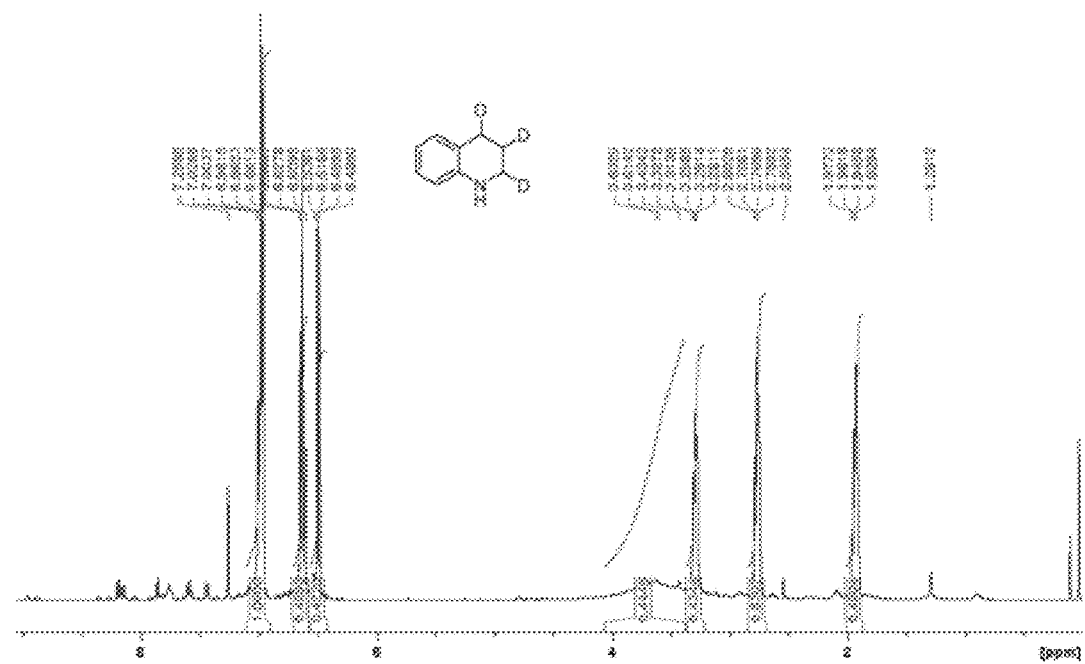
FIG. 10 shows $^1H$ NMR of Bz-THQ obtained from the Quinoline hydrogenation in $D_2O$.
Figure 11:
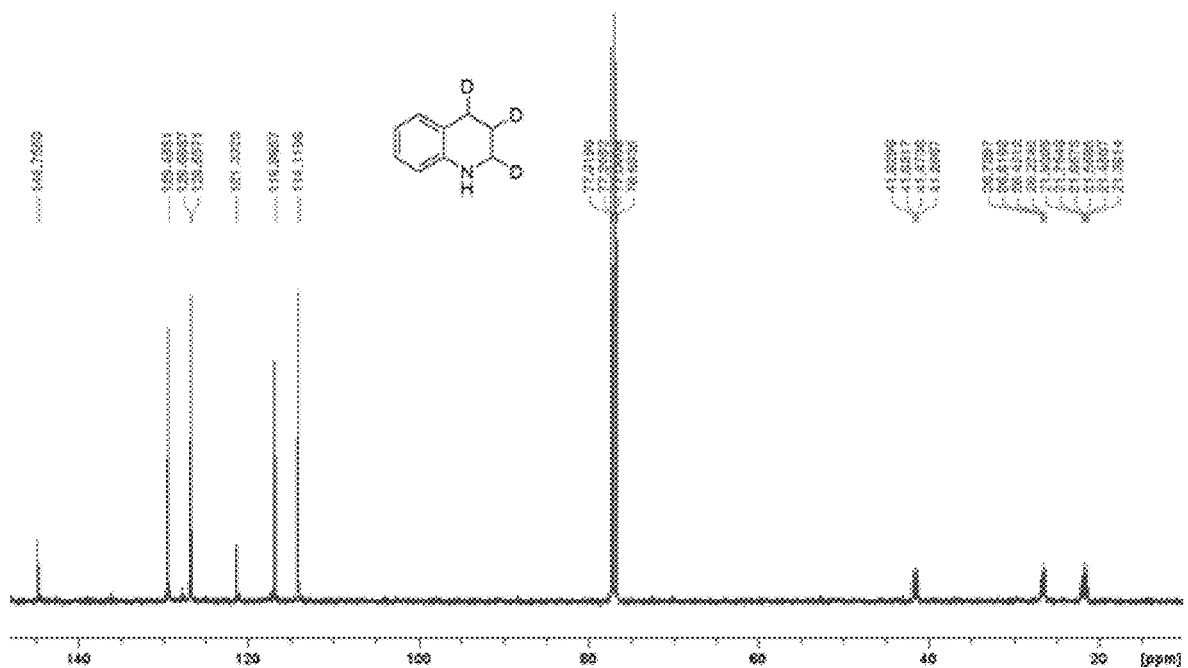
FIG. 11 shows $^{13}C$ NMR of Bz-THQ obtained from the Quinoline hydrogenation in $D_2O$.

The morphological and nanostructural features of Fe$_3$O$_4$ and Rh@Fe$_3$O$_4$ particles were investigated by transmission electron microscopy (TEM), which revealed the formation of well-dispersed spherical particles of about 7-9 nm in size with narrow size distribution (FIGS. 3a-g), which was confirmed by measurement with a particle size analyzer (FIG. 3d). Furthermore, the surface magnetite (7-9 nm; FIG. 3a) is uniformly decorated with Rh particles that are <1 nm in size (Figure. 3b); as corroborated by the confined area of elemental mapping (see FIGS. 6a and 6b). It is reasonable to assume that during the process of decorating the magnetite with Rh particles, increase in surface potential led to decrease in the size of the Rh particles to the sub-nano region. The scanning tunneling electron microscopy (STEM) was used to investigate the local physical and electronic structure of surfaces, which led to the identity of Rh particles in the sample (FIG. 2e and FIG. 7). The HRTEM image (FIG. 2f) confirms high crystallinity of $Fe_3O_4$ nanoparticles, which was also concluded from the powder XRD pattern shown earlier in FIG. 2. FIG. 2f and the Bragg reflections in the corresponding SAED pattern (FIG. 2g) yielded a d-value of 0.249 nm which could be assigned to the <311> reflection of magnetite in the specimen in cubic phase. However, ICP-OES data demonstrates that the ratio of Fe/Rh was found to be 94:6 which was further confirmed by both EDS studies, SEM and TEM. FTIR of Rh@Fe3O4 showed a vibrational red shift of 7 nm from 586 nm for the Fe—O bond in the parent magnetite.

Figure 4A:
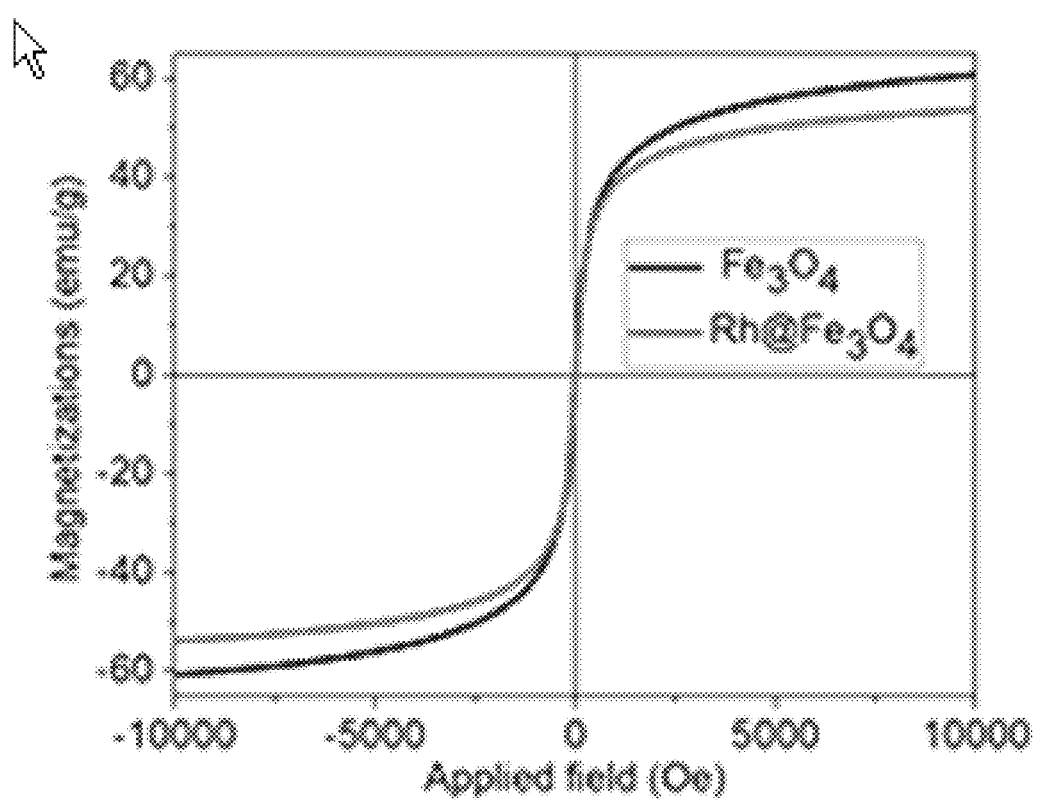
FIG. 4a shows magnetic hysteresis loops of Rh@$Fe_3O_4$ at room temperature with 1 tesla magnet.

The magnetization (M) vs. applied magnetic field (H) measurements was conducted by vibrating sample magnetometery at room temperature. FIG. 4a shows that both samples of $Fe_3O_4$ and $Rh@Fe_3O_4$ display superparamagnetic behavior as no hysteresis loop was observed in the recorded curve. It is important to highlight that slight reduction of saturation magnetization establishes the viability of the surface decoration with non-magnetic element, Rh.

From the foregoing discussion, it is clear that the reported preparation technique offers an excellent pathway to designing catalysts with well-dispersed sub-nanometer Rh particles on nanostructured magnetic support and can be extended to other solid surfaces to develop catalysts for other organic transformations.

Example 6

Catalytic Reduction:

The conversion and regioselectivity of the reduction of quinoline catalyzed by $Rh@Fe_3O_4$ was evaluated as a model reaction for the reduction of N-heterocyclic compounds. Efficacy of the magnetic catalyst towards reduction was tested by using tetrahydroxydiboron (THDB) and hydrogen gas as examples of reducing agents.

(a) $Rh@Fe_3O_4$-Catalyzed Reduction of Quinolone with THDB:

No reduction product was observed from a reaction mixture comprising quinolone and without teterhydroxydiboron. Thus, the combination of $Rh@Fe_3O_4$ and a reducing agent such as tetrahydroxydiboron is required to carry out the reduction process. Table 1 summarizes the experimental parameters and the results of quinoline hydrogenation in various media.

Scheme 1 Quinoline reduction in water

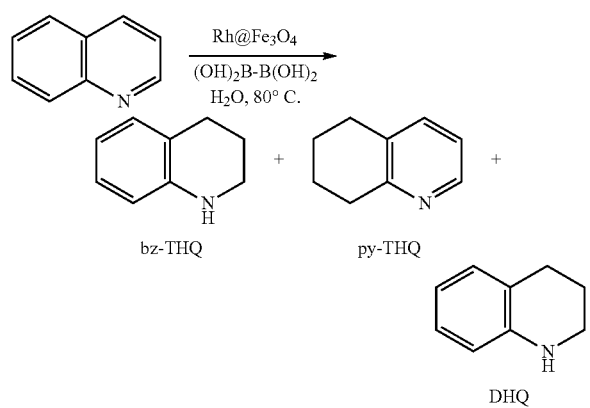

TABLE 1

$Rh@Fe_3O_4$-mediated hydrogenation of quinoline[a] using THDB as $H_2$ source

| Entry | Solvent | Temp (° C.) | Time (min.) | Conversion[b] (%) | Selectivity[c] (%) |
|---|---|---|---|---|---|
| 1 | Water | Rt | 30 | — | — |
|  |  | 50 | 10 | 88 | 100 |
|  |  |  | 20 | 94 | 100 |
|  |  | 80 | 10 | >99 | 100 |
| 2 | IPA | 80 | 10 | 15 | 100 |
|  |  |  | 60 | 67 | 100 |
|  |  |  | 300 | 94 | 100 |
| 3 | THF | 80 | 300 | — | — |
| 4 | Cyclohexane | 80 | 300 | — | — |
| 5 | Methanol | 80 | 300 | nd | nd |
| 6 | 1,4-dioxane | 80 | 300 | — | — |

[a]0.5 mmol of quinoline, 4 mmol of THDB in 2 mL water were used;
[b]measured by GC;
[c]identified by GC-MS and NMR;
rt: room temperature;
nd: not determined.

Scheme 1 shows the possible reaction products of quinoline reduction using tetrahydroxydiboron in water. To explore the catalytic reduction activity of $Rh@Fe_3O_4$, quinoline and THDB were selected as a model nitrogen heterocyclic reactant and reducing agent, respectively (Table 1). Samples were taken out periodically and analyzed by thin layer chromatography (TLC) and gas chromatography (GC) to evaluate conversion and selectivity. Based on preliminary results, the reaction solvent, time, temperature, amount of catalyst, and the concentrations quinolone and THDB were optimized. Reduction reactions were carried out in water, IPA, methanol, THF, 1,4-dioxane and cyclohexane, and the results are summarized in Table 1. No reduction product was observed in methanol, dioxane, cyclohexane and THF even after long reaction time for up to five hours (Table 1). The reaction progress in IPA was much slower than in water and was completed in 5 h. In contrast, quantitative conversion quinolone to reduced product was observed in water. Also, the effect of temperature was briefly examined. In water, no conversion was observed at room temperature, but the conversion was appreciable at 50 and 80° C. (Table 1). In fact, it took only 10 min. at 80° C. to achieve >99% conversion with 100% selectivity. The product selectivity was maintained even at 80° C. (see Table 1). The effect of relative concentration of tetrahydroxydiboron (THDB) on quinoline reduction in water is shown in Table 2. The amount of THDB was varied systematically from 2 to 8 molar equivalent of quinoline. The conversion was observed to increase steadily with increasing THDB and 97% conversion into bz-THQ was achieved with 6 equivalents THDB after 30 min. of reaction time. But the optimum conversion of ~99% was achieved with 8 equivalent of THDB (Table 2) in just 10 min. Hence, quinoline can be smoothly reduced to bz-THQ in water at 80° C. by adding eight equivalent of tetrahydroxydiboron as reducing agent to selectively produce Bz-THQ in 10 minutes without any other products. In contrast, bz-THQ, py-THQ and DHQ have been observed in a conventional hydrogenation.

The reduction of heterocyclic rings in comparison to carbocyclic rings depends on the nature of interaction of quinoline with the metal center of the catalyst (Konnerth et al. and Xia et al.—each incorporated herein by reference in their entirety). The observed exclusive regioselectivity for the reduction of the heterocyclic aromatic ring could be explained by quinoline interaction with or absorption to the active metal through the ring nitrogen, which can impact the instantaneous microenvironment generated around the metal center [Shaikh et al. RSC Adv., 2016, 6, 41687-41695—incorporated herein by reference in its entirety]. The interaction between the ring nitrogen and the metal ion is enhanced by the basic nature of the support which plays an essential role in directing the reaction pathway [Pinna et al. Chem. Mater., 2005, 17, 3044-3049—incorporated herein by reference in its entirety]. Earlier reports described that hydroxylated basic supports, such as magnesium oxide or magnetite, have been shown to be capable of engaging N-bearing heterocyclic moieties via hydrogen bonding [Deraedt et al. J. Am. Chem. Soc. 2017, 139, 18084-18092; Sanchez et al. Applied Catalysis A: General 477 (2014) 117-124; and Bai et al. Angew. Chem., Int. Ed. 2016, 55, 15656-15661—each incorporated herein by reference in their entirety].

TABLE 2

Effect of the relative concentration of tetrahydroxydiboron (THDB) on quinoline[a] hydrogenation in water as a function of on-stream reaction time.

| Entry | THDB (mmol) | Time (min) | Conv.[b] (%) | Sel.[c] (%) |
|---|---|---|---|---|
| 1 | 2 | 10 | 57 | 100 |
|   |   | 20 | 59 | 100 |
|   |   | 30 | 64 | 100 |
| 2 | 4 | 10 | 62 | 100 |
|   |   | 20 | 87 | 100 |
|   |   | 30 | 93 | 100 |
| 3 | 6 | 10 | 96 | 100 |
|   |   | 20 | 97 | 100 |
|   |   | 30 | 97 | 100 |
| 4 | 8 | 10 | >99 | 100 |

[a]substrate 1 mmol;.
[b]measured by GC;
[c]identified by GC-MS and NMR.

(b) Rh@Fe$_3$O$_4$-Catalyzed Reduction of Quinolone with Hydrogen Gas:

The catalytic performance of Rh@Fe$_3$O$_4$ catalyst towards the reduction of a series of N-heterocyclic compounds with hydrogen gas was evaluated in water and THF as well as without a solvent. The reaction variables and the results are summarized in Table 3. Initially, the reaction conditions were improved using quinoline as model substrate with various solvents, pressures, and temperatures. The solvent has a large effect on the reduction-catalyzed reaction. Quinoline is reduced in 2 h to bz-THQ (Scheme 1) in water under 20 bar hydrogen pressure. In less polar solvent such as toluene and methanol, a significant decrease in conversion was observed (Table 3). At room temperature, no detectable product was observed (Table 3). But on increasing the temperature to 50° C., quinoline was quantitatively converted to bz-THQ. The effect of pressure on the conversion and selectivity were studied and summarized. At 115° C., neat pyridine was converted quantitatively to piperidine in 10 h. Similar results were observed in the hydrogenation of pyrazine in IPA (Table 3). Also, the hydrogenation activity of the catalyst was evaluated for the five-membered ring heterocycles (Table 3), and pyrrole was found to be the most reactive among the hetrocyclic compounds tested (Table 3). At 130° C./40 bar, indole hydrogenation attained 70% conversion with 100% selectivity after 24 h in THF, whereas only 12% of 2-methylindol is converted to the hydrogenation product at 150° C./40 bar in 24 h of reaction time. This observation could be partly ascribed to the presence of electron-donating group in the 5-membered ring that tends to increase the electron density around nitrogen atom, thereby effectively binding its lone pair with Rh metal in the catalyst, causing deactivation of the active metal centers.

TABLE 3

Rh@Fe$_3$O$_4$-mediated hydrogenation of N-heteroarene by hydrogen gas

| Entry | Substrate[a] | Product | Solv. | Time (h) | Temp (°C.) | Pres. (bar) | Conv.[b] (%) | Sel..[c] (%) |
|---|---|---|---|---|---|---|---|---|
| 1 | 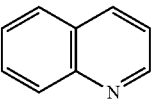 | 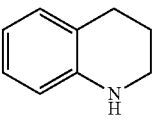 | Water | 2 | rt | 20 | — | — |
|   |   |   |   | 2 | 40 | 20 | >67 | 100 |
|   |   |   |   | 2 | 50 | 20 | >99 | 100 |
| 2 | 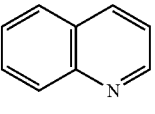 | 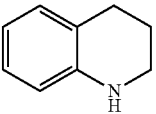 | Methanol | 2 | 50 | 30 | 61 | 100 |
| 3 | 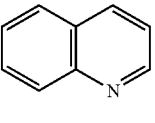 | 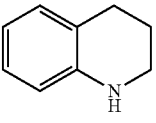 | Toluene | 2 | 50 | 30 | 36 | 100 |
| 2[d] |  | 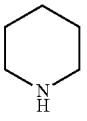 | None | 10 | 115 | 40 | >99 | 100 |

TABLE 3-continued

Rh@Fe₃O₄-mediated hydrogenation of N-heteroarene by hydrogen gas

| Entry | Substrate[a] | Product | Solv. | Time (h) | Temp (°C.) | Pres. (bar) | Conv.[b] (%) | Sel.[c] (%) |
|---|---|---|---|---|---|---|---|---|
| 3[e] |  | 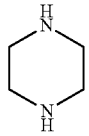 | IPA | 14 | 130 | 30 | >99 | 100 |
| 4 |  |  | None | 10 | 120 | 30 | >97 | 100 |
| 5 | 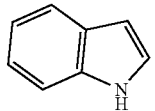 | 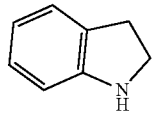 | THF | 24 | 140 | 40 | 70 | 100 |
| 6 | 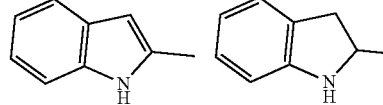 | 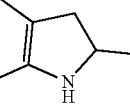 | THF | 24 | 150 | 40 | 12 | 100 |

[a]amount of substrate used 0.5 mmol;
[b]measured by GC;
[c]identified by GC-MS and NMR;
[d]substrate used 12 mmol, 1 mL;
[e]substrate used 6 mmol.

Hydrogenation of aromatic compounds such as benzene, toluene, xylenes and the like were carried out with pressurized hydrogen gas without any solvent. Again, the reaction temperature is an important determining factor for driving the reaction toward formation of the reduction product. For instance, it was observed that benzene could be rapidly hydrogenated to cyclohexane at 100° C. and a pressure of 30 bar (Table 4). At 115° C. and 50 bar hydrogen gas pressure, 51% of toluene was converted to methylcyclohexane in 24 hours, and the conversion is increased to 70% when temperature was raised to 130° C. The observed increased activity implies that the catalyst is stable at higher temperature. In the case of p-xylene, the hydrogenation propensity decreased relative to toluene due to the increase of methyl substituents (Table 4). Only 22% conversion of p-xylene to 1,4-dimethyl cyclohexane was observed in 24 hours.

TABLE 4

Rh@Fe₃O₄-mediated hydrogenation of aromatic compounds by hydrogen gas without solvent

| Entry | Substrate | Product | Time (h) | Conv. (%) | Sel. (%) |
|---|---|---|---|---|---|
| 1 | Benzene | Cyclohexane | 8 | >99 | 100 |
| 2 | Toluene | Methycyclohexane | | 51 | 100 |
| | | | 24 | 70 | 100 |
| 3 | p-Xylene | 1,4-Dimethylcyclohexane | 24 | 22 | 100 |

[a]measured by GC;
[b]identified by GC-MS;
[c]used 1 mL benzene;
[d]used 0.5 mL toluene and p-xylene.

Based on the observed activity and selectivity of the catalyst, a reaction pathway is proposed in Scheme 2. Deuterium isotope labelling studies were performed by using D₂O as and identifying the location of additional hydrogen in the hydrogenated quinoline.

Scheme 2 Isotopic mechanistic experiment

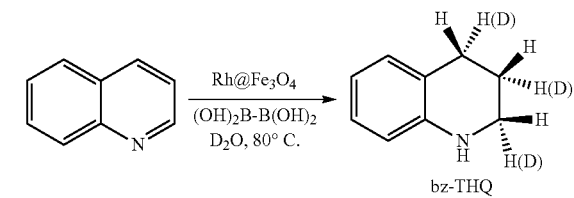

Figure 12A:
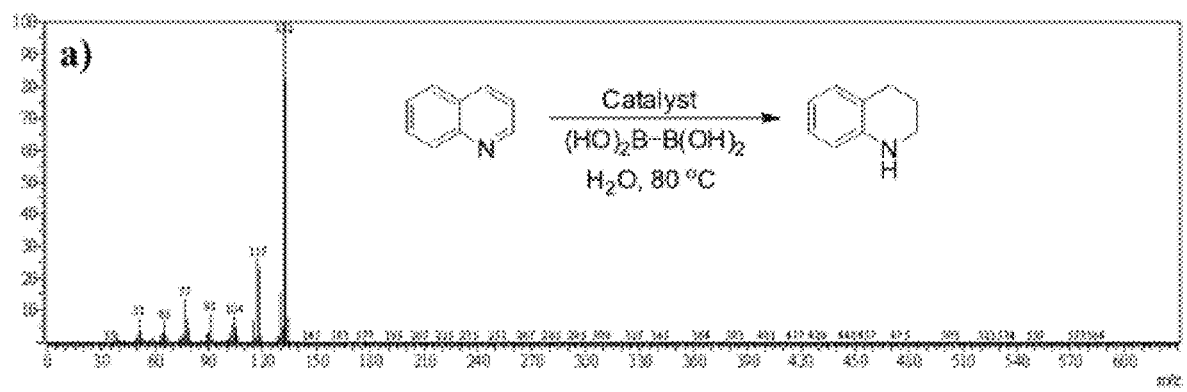
FIG. 12a shows MS spectra of reduced product bz-THQ in presence of tetrahydroxydiboron in $H_2O$.
Figure 12B:
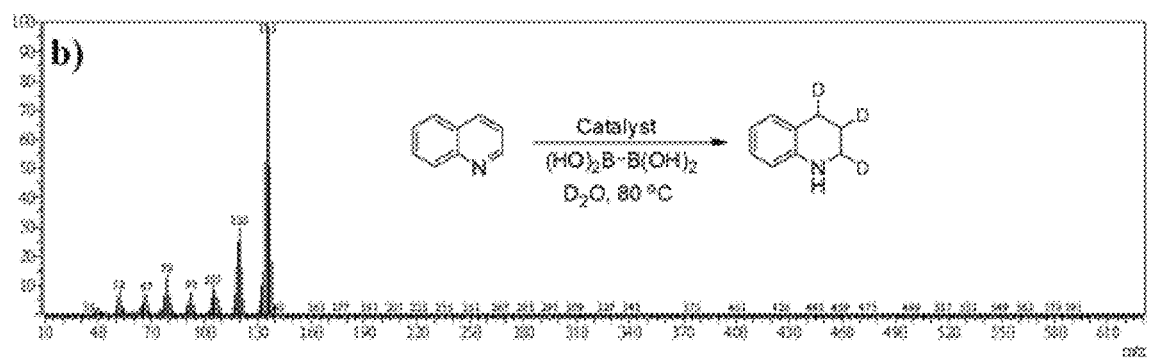
FIG. 12b shows MS spectra of reduced product deuterated Bz-THQ in presence of tetrahydroxydiboron in $D_2O$.

Mass spectrometric and NMR spectroscopic studies indicated that quinoline was deuterated at the C(2), C(3) and C(4) positions of the N-bearing heterocyclic ring (see FIGS. 8-11). Also, nitrogen should be deuterated. However, the possibility of rapid exchange of deuterium with water during the process of isolating the product precluded the observation of deuterated nitrogen (see FIGS. 12a and 12b)) [Mao et al. *J. Mol. Catal. A: Chem.* 2011, 341, 51-56—incorporated herein by reference in its entirety]. From the foregoing discussion, it is evident that quinoline can be quantitatively and selectively reduced to bz-THQ in water by THDB. Also, the results highlight the definite role of water molecules in the hydrogenation process. On the basis of above discussion, we propose a plausible route for the catalytic hydrogenation of quinoline in the following sequence (Scheme 3).

Scheme 3 is a proposed mechanism for quinolone reduction with THDB catalyzed by Rh@Fe₃O₄ Initially, Rh undergoes oxidative addition to THDB to produce 1, followed by the coordination of water molecule to boron atom to form adduct 2. The Rh-hydride complex 3 is produced by the elimination of boric acid ($H_3BO_3$). Quinoline which is in contact with the magnetite support through hydrogen bonding, enter into the catalytic cycle and forms intermediate 4.

catalytic reaction scheme, at least four equivalents of water molecules are required for the hydrogenation of one molecule of quinoline, producing bz-THQ.

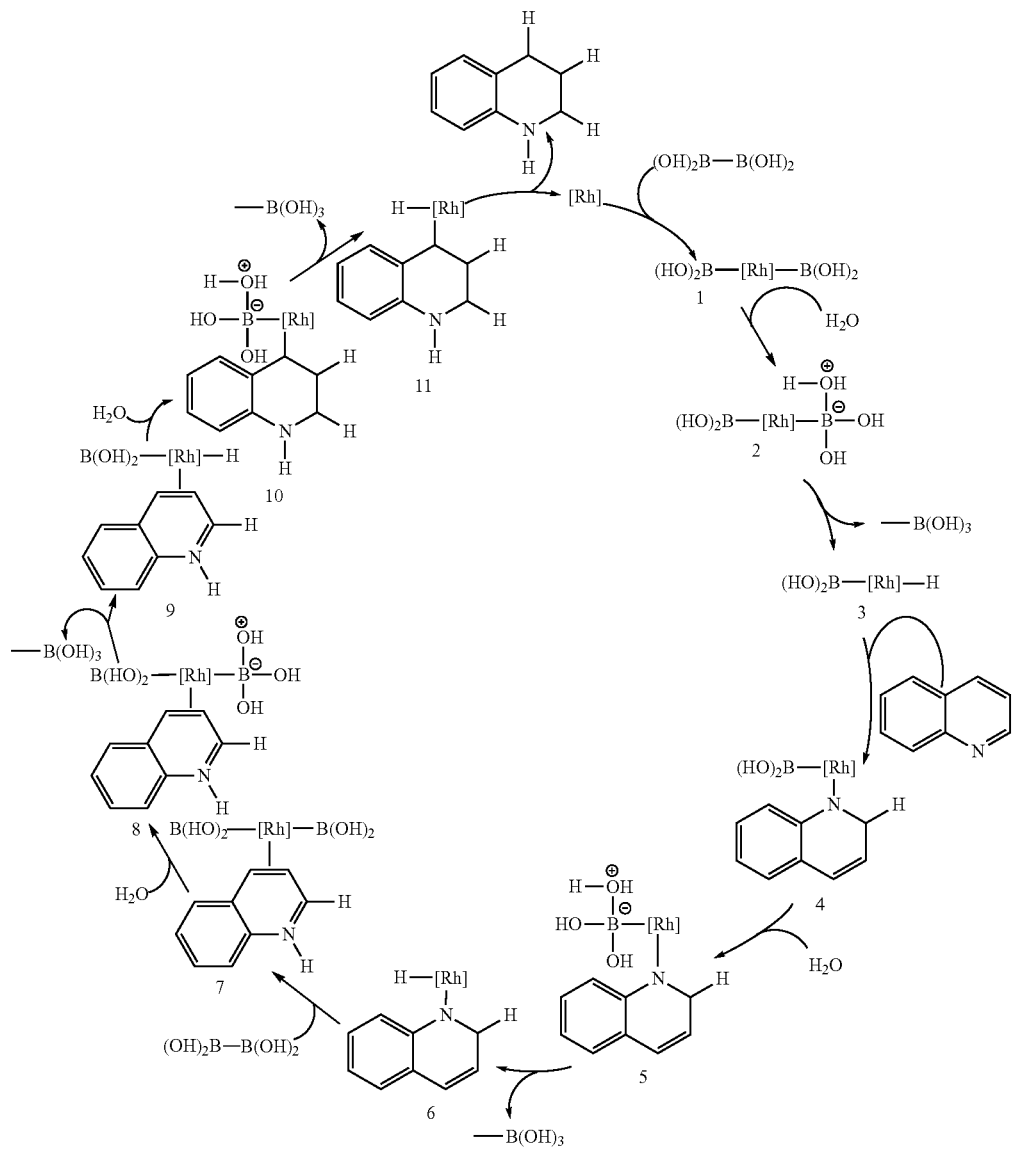

Figure 4B:
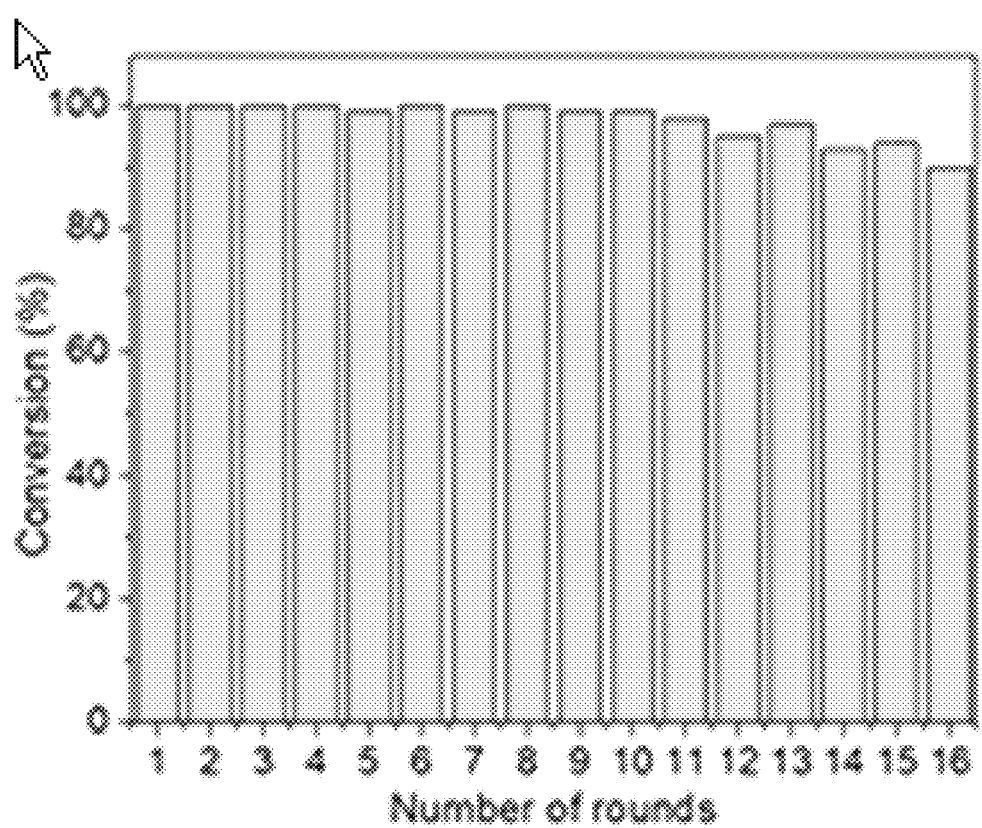
FIG. 4b shows recycling the catalyst in the hydrogenation reaction of quinoline at 50° C. in water.
Figure 13:
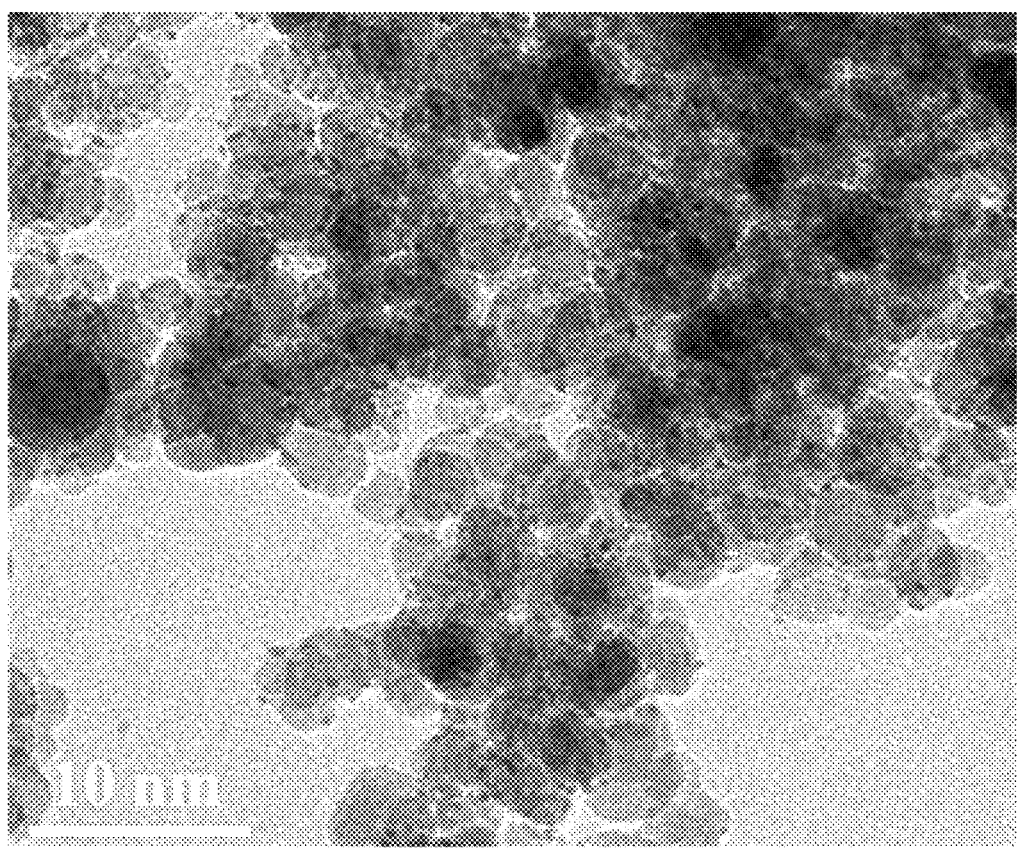
FIG. 13 shows TEM image of $Fe_3O_4$@Rh after 16 consecutive catalytic cycles.

Scheme 3 Proposed catalytic cycle for the reduction of quinoline in water with THD The intermediate is formed by the transfer of hydrogen from Rh-hydride to C(2) of quinolone, the most electrophilic center in quinolone leading to the reduction of C(2)-N bond [Dell'Anna et al. *J. Mol. Catal A: Chem.* 2015, 402, 83-91—incorporated herein by reference in its entirety]. Since the reduction of the C2-N bond disrupts the aromaticity of the heterocyclic ring, the reduction of C2-N is probably the rate determining step [Eros et al. *Chem. Eur. l* 2012, 18, 574-585]. Coordination of THDB to Rh particles produces 7 followed by addition of another water molecule to a boron atom of THDB generates produces intermediate 8, and another hydrogen transfer and liberating boric acid to produces 9. Elimination of boric acid from 9 to produce 11 which rearranges to produce 1,2,3,4-tetrahydroquinolin (bz-THQ) and free Rh. As can be readily seen from the proposed To examine recycling the catalyst in subsequent hydrogenation reactions, the catalyst was isolated from a reaction mixture for reduction of quinolone and recycled. After each reduction cycle, the catalyst was removed from the reaction mixture by putting a magnet at the bottom of the flask and decanting the liquid. The catalyst was thoroughly washed several times with methanol and dichloromethane, and dried for use in subsequent reduction cycles without adding any fresh catalyst. It was found that the catalyst could be used in 16 consecutive cycles without significant loss of catalytic activity. The catalytic activity declined slightly with increasing the number of cycles as about 93% of the catalytic activity was observed after 16 cycles (FIG. 4b). The used catalyst was collected at the end of cumulative cycles and the metal content was quantified by ICP-OES. The used catalyst showed 6.1% loss of Rh as a result of leaching from the surface of magnetic nanoparticles. This was corroborated by the HRTEM and STEM investigations on the recycled catalyst, which showed no severe damage to the magnetite surface; no sign of surface agglomeration was observed either (see FIG. 13).

The disclosure describes a facile synthesis of sub-nano sized Rh particles supported on superparamagnetic iron oxide nanoparticles (SPIONs, $Fe_3O_4$), for efficient hydrogenation and of a series of N-bearing heterocyclic and carbocyclic aromatic compounds under mild experimental conditions in environmentally friendly solvent such as water. The results showed that the regioselective reduction of quinoline in water was complete in about 10 min. using THDB as the hydrogen source. The Rh@ $Fe_3O_4$ construct was a stable and versatile catalyst in the reduction of other aromatic and heterocycles compounds, such as but not limited to pyridine, pyrazine, indole, benzene, toluene, and xylene with hydrogen gas under moderate pressure and temperature. Isotopic labelling studies were successfully revealed the source of hydrogen and the role of THDB in the reaction. The catalyst was shown to possess excellent activity towards reduction reaction for 16 consecutive cycles. The combination of water as a green solvent and tetrahydroxydiboron as reducing agent offers an environmentally benign synthesis strategy for industrial relevant compounds

The invention claimed is:

1. A hydrogenation method for an N heterocyclic aromatic ring comprising:
    suspending a catalyst in a compound comprising the N-heterocyclic aromatic ring to form a catalyst mixture, wherein the catalyst consists of superparamagnetic iron oxide nanoparticles (SPIONs) and rhodium particles of less than 1 nm deposited on the SPIONs,
    mixing the catalyst mixture with tetrahydroxydiboron (THDB), and
    heating to a temperature in the range of 40 to 100° C. to hydrogenate the N-heterocyclic aromatic ring.

2. The method of claim 1, wherein the N-heterocyclic aromatic ring is selected from the group consisting of pyrrole, pyridine, pyrazol, imidazole, triazol, tetrazol, indole, quinoline, isoquinoline, pyrimidine, pyridazine, pyrazine, purine, oxazol, thiazol, isothiazol, 1,2-oxazine, 1,3-oxazine, 1,4-oxazine, 1,2-thiazine, 1,3-thiazine, 1,4-thiazine, 1,2,3-triazine, 1,2,4-triazine, and 1,3,5-triazine.

* * * * *